US009207250B2

(12) United States Patent
Asahara et al.

(10) Patent No.: US 9,207,250 B2
(45) Date of Patent: Dec. 8, 2015

(54) REAGENT PREPARING DEVICE, REAGENT PREPARING METHOD AND SPECIMEN PROCESSING SYSTEM

(75) Inventors: Tomoyuki Asahara, Kobe (JP); Koichi Okubo, Kobe (JP); Noriyuki Nakanishi, Kakogawa (JP)

(73) Assignee: SYSMEX CORPORATION, Kobe-Shi (JP)

( * ) Notice: Subject to any disclaimer, the term of this patent is extended or adjusted under 35 U.S.C. 154(b) by 369 days.

(21) Appl. No.: 12/730,557

(22) Filed: Mar. 24, 2010

(65) Prior Publication Data

US 2010/0248289 A1    Sep. 30, 2010

(30) Foreign Application Priority Data

Mar. 27, 2009    (JP) ................. 2009-079329

(51) Int. Cl.
*G01N 1/00*      (2006.01)
*G01N 35/00*     (2006.01)

(52) U.S. Cl.
CPC .......... *G01N 35/00663* (2013.01); *G01N 2035/00673* (2013.01)

(58) Field of Classification Search
CPC ............. G01N 35/00663; G01N 2035/00673
USPC ................. 422/62, 63, 68.1; 702/25
See application file for complete search history.

(56) References Cited

U.S. PATENT DOCUMENTS

| 5,800,056 A | 9/1998 | Suzuki et al. |
| 2004/0057872 A1 | 3/2004 | Shibuya et al. |
| 2006/0030049 A1 | 2/2006 | Bhimani et al. |
| 2010/0161243 A1* | 6/2010 | Nagai et al. ............. 702/25 |

FOREIGN PATENT DOCUMENTS

| JP | 63-138268 A | 6/1988 |
| JP | 01-167660 A | 7/1989 |
| JP | 06-207944 A | 7/1994 |
| WO | WO 2009/031461 A1 | 3/2009 |

* cited by examiner

*Primary Examiner* — Timothy Cleveland
(74) *Attorney, Agent, or Firm* — Brinks Gilson & Lione

(57) ABSTRACT

A reagent preparing device for preparing a reagent to be supplied to a measurement section for measuring a specimen; the reagent preparing device comprising: a reagent preparing section for preparing a reagent including a first liquid and a second liquid, different from the first liquid; a reagent storage container, connected to the measurement section, for storing the reagent prepared by the reagent preparing section; and a controller configured for determining whether or not the reagent stored in the reagent storage container is suppliable to the measurement section based on reagent expiration date information related to an expiration date of the reagent stored in the reagent storage container, is disclosed. A reagent preparing method and a specimen processing system are also disclosed.

12 Claims, 21 Drawing Sheets

US 9,207,250 B2

REAGENT PREPARING DEVICE, REAGENT PREPARING METHOD AND SPECIMEN PROCESSING SYSTEM

RELATED APPLICATIONS

This application claims priority under 35 U.S.C. §119 to Japanese Patent Application No. 2009-079329 filed on Mar. 27, 2009, the entire content of which is hereby incorporated by reference.

FIELD OF THE INVENTION

The present invention relates to reagent preparing devices, reagent preparing methods, and specimen processing systems, and in particular to a reagent preparing device, a reagent preparing method, and a specimen processing system capable of preparing a reagent to use in the measurement of a specimen.

BACKGROUND OF THE INVENTION

A reagent preparing device capable of preparing a reagent to use in the measurement of a specimen is conventionally known (see e.g., Japanese Laid-Open Patent Publication No. 1-167660).

Japanese Laid-Open Patent Publication No. 1-167660 discloses a reagent preparing device capable of preparing a reagent to use in the measurement by an analysis instrument by mixing concentrated solution and pure water in a stirring tank.

An automatic analyzer capable of monitoring an expiration date of the reagent is also conventionally known (see e.g., US Patent Application Publication 2004-057872).

US Patent Application Publication 2004-057872 discloses an automatic analyzer for aspirating a reagent from a reagent cassette on a reagent table arranged at a predetermined aspiration position, and measuring a specimen using the aspirated reagent. The automatic analyzer is configured to monitor the expiration date of the reagent accommodated in the reagent cassette on the reagent table, and discharging the reagent cassette accommodating the relevant reagent from the reagent table if the reagent is expired.

In order to enhance the reliability of the analysis result of the specimen, the reagent is preferably used within a predetermined expiration date after being prepared. However, in Japanese Laid-Open Patent Publication No. 1-167660, a technique for using the prepared reagent within the expiration date is not disclosed nor suggested. Furthermore, US Patent Application Publication 2004-057872 describes an automatic analyzer for monitoring the expiration date of the reagent accommodated in the reagent cassette on the reagent table, but does not disclose nor suggest applying the monitoring of the expiration date of the reagent to the reagent preparing device.

SUMMARY OF THE INVENTION

The scope of the present invention is defined solely by the appended claims, and is not affected to any degree by the statements within this summary.

A first aspect of the present invention is a reagent preparing device for preparing a reagent to be supplied to a measurement section for measuring a specimen; the reagent preparing device comprising: a reagent preparing section for preparing a reagent including a first liquid and a second liquid, different from the first liquid; a reagent storage container, connected to the measurement section, for storing the reagent prepared by the reagent preparing section; and a controller configured for determining whether or not the reagent stored in the reagent storage container is suppliable to the measurement section based on reagent expiration date information related to an expiration date of the reagent stored in the reagent storage container.

A second aspect of the present invention is a reagent preparing method for preparing a reagent to be supplied to a measurement section for measuring a specimen, the method comprising: preparing a reagent including a first liquid and a second liquid, different from the first liquid; storing the prepared reagent in a reagent storage container connected to the measurement section; and determining whether or not the reagent stored in the reagent storage container is suppliable to the measurement section based on reagent expiration date information related to an expiration date of the reagent stored in the reagent storage container.

A third aspect of the present invention is a specimen processing system comprising: a measurement section for measuring a specimen using a reagent including a first liquid and a second liquid, different from the first liquid; a reagent preparing section for preparing the reagent; a reagent storage container, connected to the measurement section, for storing the reagent prepared by the reagent preparing section; and a controller configured for determining whether or not the reagent stored in the reagent storage container is suppliable to the measurement section based on reagent expiration date information related to an expiration date of the reagent stored in the reagent storage container.

DETAILED DESCRIPTION OF THE PREFERRED EMBODIMENTS

The preferred embodiments of the present invention will be described hereinafter with reference to the drawings.

First Embodiment

First, a configuration of a reagent preparing device 4 according to a first embodiment of the present invention will be described with reference to FIGS. 1 to 8. In the first embodiment, a case of using the reagent preparing device 4 according to the first embodiment of the present invention as one part of a blood sample processing system 1 for performing a blood test will be described.

Figure 1:
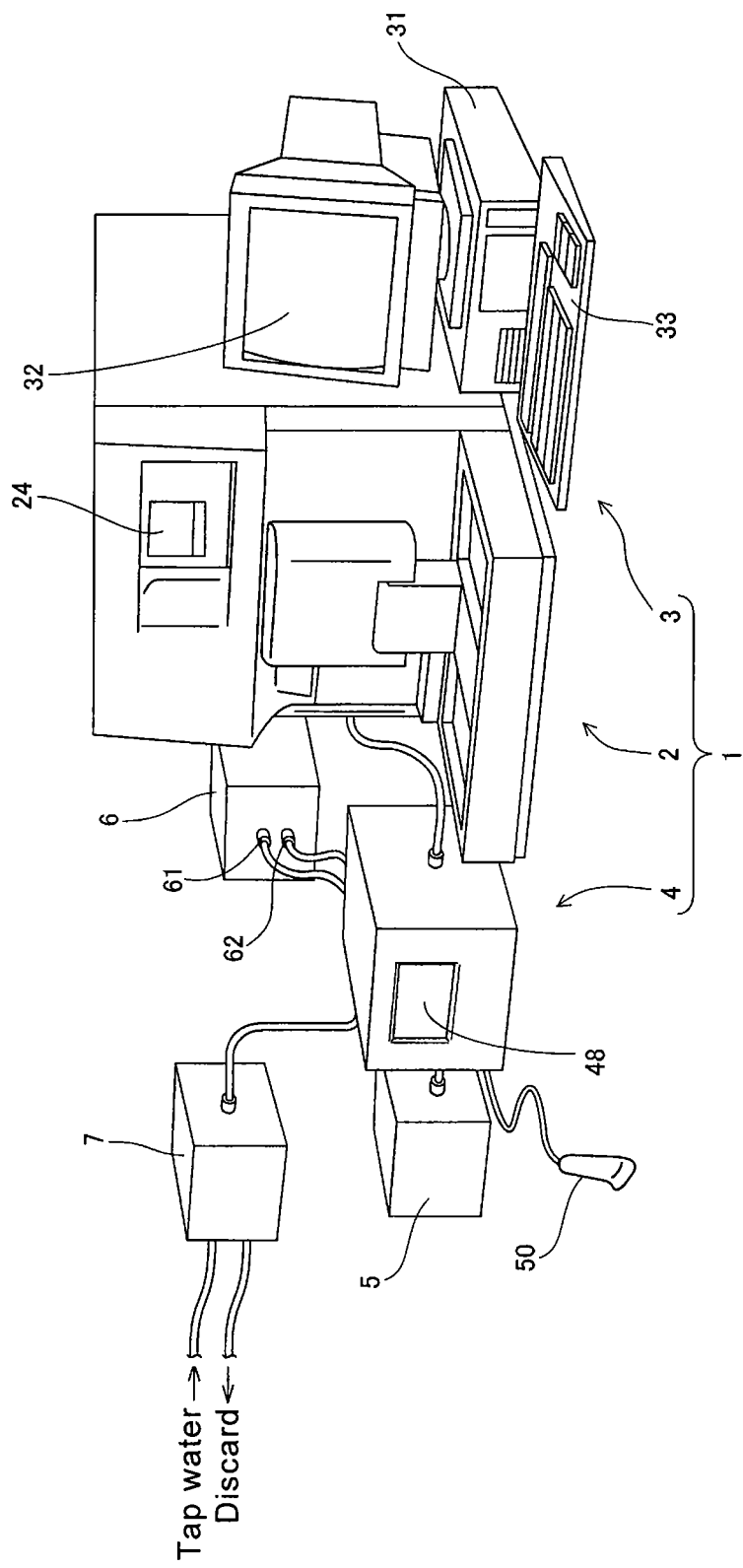
FIG. 1 is a perspective view showing a usage state of a reagent preparing device according to a first embodiment of the present invention.

As shown in FIG. 1, the blood specimen processing system 1 is configured by a measurement section 2 having a function of measuring the blood, a data processing section 3 for analyzing the measurement data output from the measurement section 2 and obtaining an analysis result, and the reagent preparing device 4 for preparing a reagent to use in the processing of a specimen. The measurement section 2 is configured to perform measurements on white blood cells, reticulocytes, and blood platelets in the blood through a flow cytometry method. The measurement section 2 is configured to dilute the blood using a reagent prepared and supplied by the reagent preparing device 4 and to perform measurements on white blood cells, red blood cells, reticulocytes, and blood platelets. The measurement section 2 is also configured to clean a sampling valve 21b, a reaction chamber 21c and the like arranged in a sample preparing unit 21, as well as a sheath flow cell 22c and the like arranged in a detection unit 22, which are to be hereinafter described, using the reagent prepared and supplied by the reagent preparing device 4 as a cleaning fluid. The flow cytometry method is a measurement method of particles (blood cells) for detecting the forward scattered light, the lateral scattered light, and the lateral fluorescence emitted by the particles (blood cells) in the measurement sample by forming a sample flow including the measurement sample and irradiating the sample flow with laser light.

Figure 2:
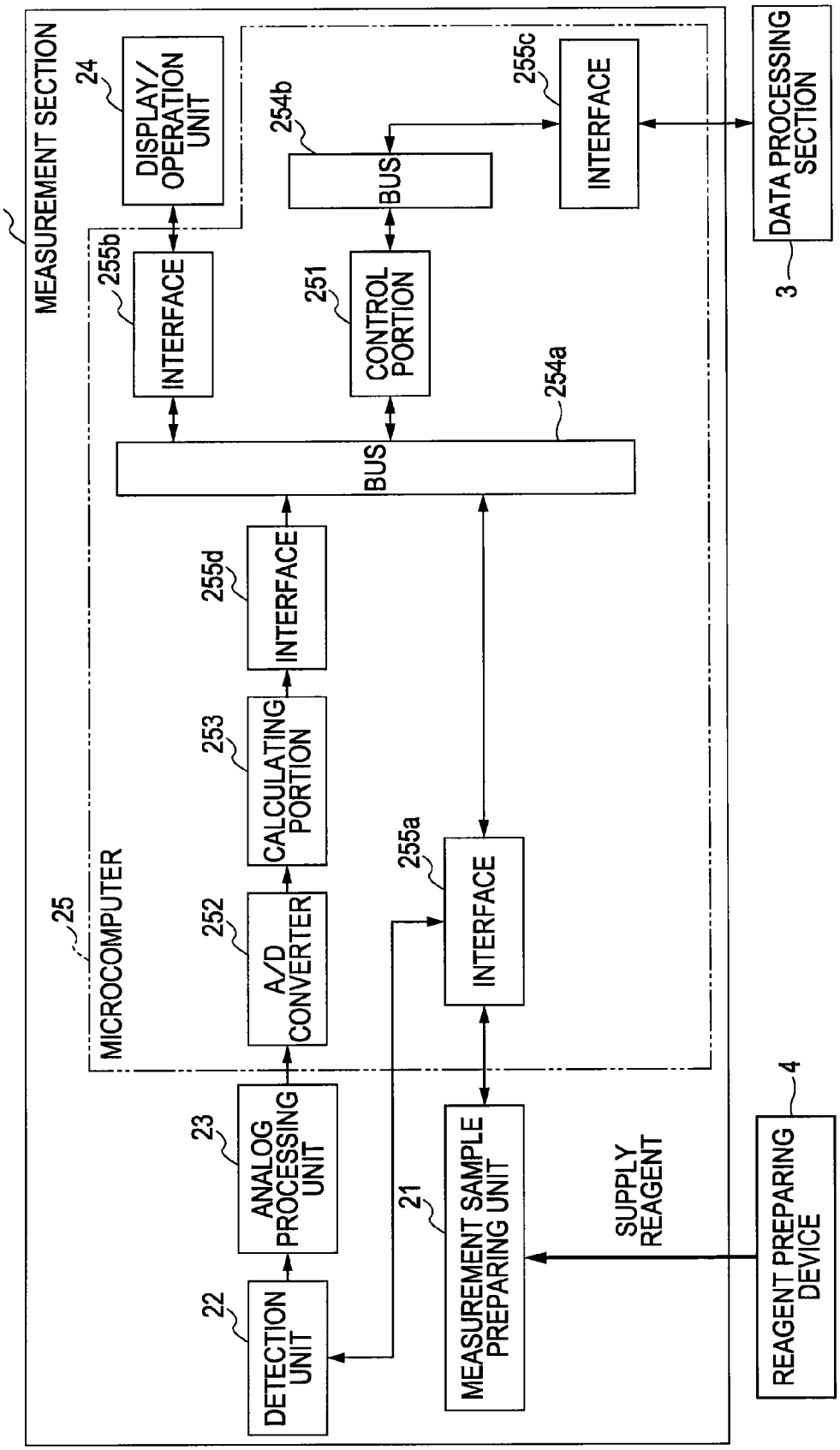
FIG. 2 is a block diagram showing a configuration of a blood specimen processing system including the reagent preparing device according to the first embodiment.

As shown in FIG. 2, the measurement section 2 includes a measurement sample preparing unit 21, a detection unit 22 for performing a measurement of the measurement sample, an analog processing unit 23 with respect to the output of the detection unit 22, a display/operation unit 24, and a microcomputer 25 for controlling the measurement section 2.

Figure 3:
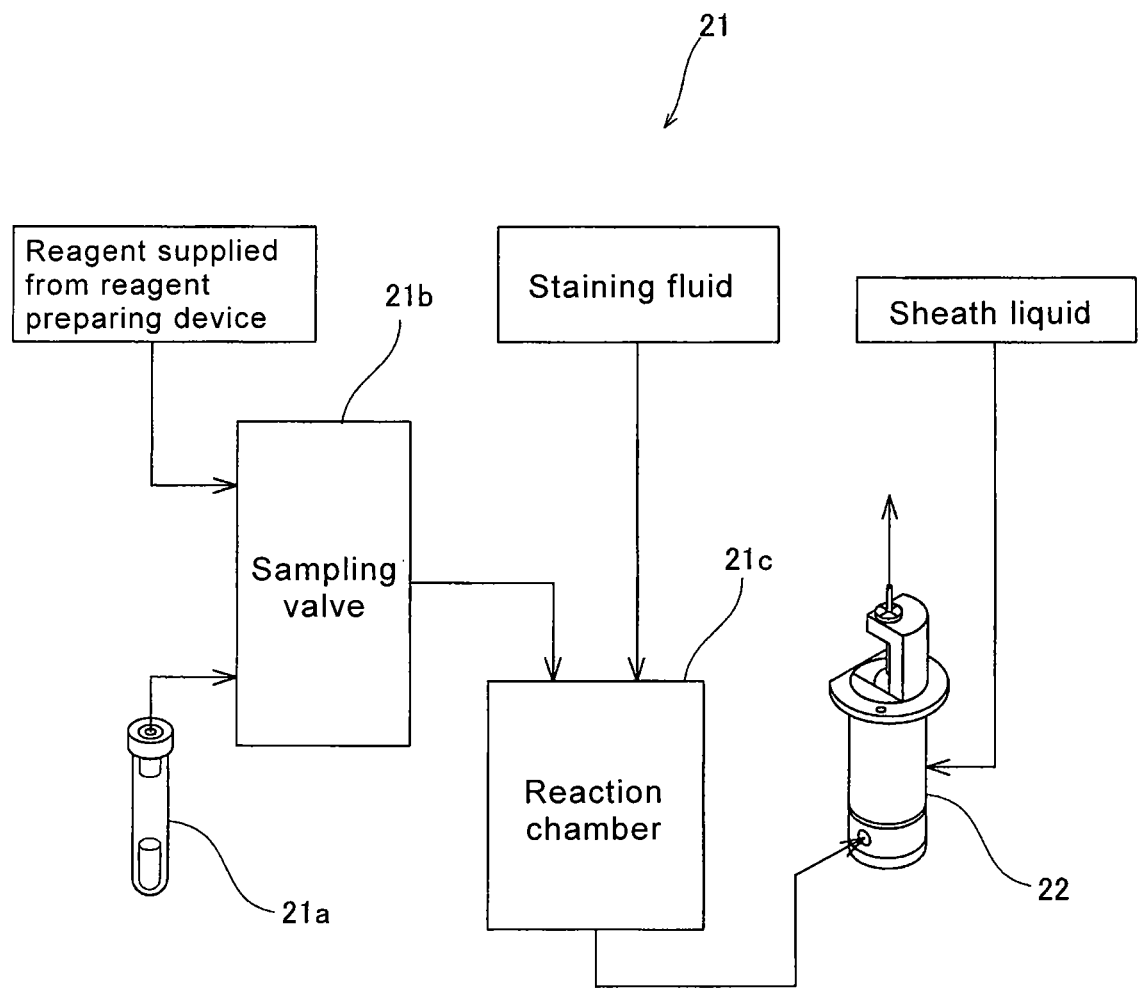
FIG. 3 is a view describing a sample preparing unit of the blood specimen processing system including the reagent preparing device according to the first embodiment shown.

The measurement sample preparing unit 21 is arranged to prepare a white blood cell measurement sample, a reticulocyte measurement sample, and a blood platelet measurement sample. As shown in FIG. 3, the measurement sample preparing unit 21 includes the sampling valve 21b for aspirating blood and the reaction chamber 21c. A blood collecting tube 21a stores the blood to be analyzed.

The sampling valve 21b has a function of quantifying the blood of the blood collecting tube 21a aspirated by an aspiration pipette (not shown) by a predetermined amount. The sampling valve 21b is configured so that a predetermined reagent can be mixed with the aspirated blood. That is, the sampling valve 21b is configured so that a diluted sample in which a predetermined amount of reagent supplied from the reagent preparing device 4 is mixed in a predetermined amount of blood can be generated.

The reaction chamber 21c is configured so that a predetermined staining fluid is further mixed to the diluted sample supplied from the sampling valve 21b and reacts with it for a predetermined time. The measurement sample preparing unit 21 thus has a function of preparing the white blood cell measurement sample in which the white blood cells are stained and the red blood cells are hemolyzed. The measurement sample preparing unit 21 also has a function of preparing the reticulocyte measurement sample in which the reticulocyte is stained and a function of preparing the blood platelet measurement sample in which the blood platelet is stained.

The measurement sample preparing unit 21 is also configured to supply the white blood cell measurement sample with the sheath liquid from the measurement sample preparing unit 21 to the sheath flow cell 22c described later (see FIG. 4) at the time of a white blood cell differential measurement (hereinafter also referred to as "DIFF measurement") mode. The measurement sample preparing unit 21 is also configured to supply the reticulocyte measurement sample with the sheath liquid from the measurement sample preparing unit 21 to the sheath flow cell 22c at the time of a reticulocyte measurement (hereinafter also referred to as "RET measurement") mode. Furthermore, the measurement sample preparing unit 21 is also configured to supply the blood platelet measurement sample with the sheath liquid from the measurement sample preparing unit 21 to the sheath flow cell 22c at the time of a blood platelet measurement (hereinafter also referred to as "PLT measurement") mode.

Figure 4:
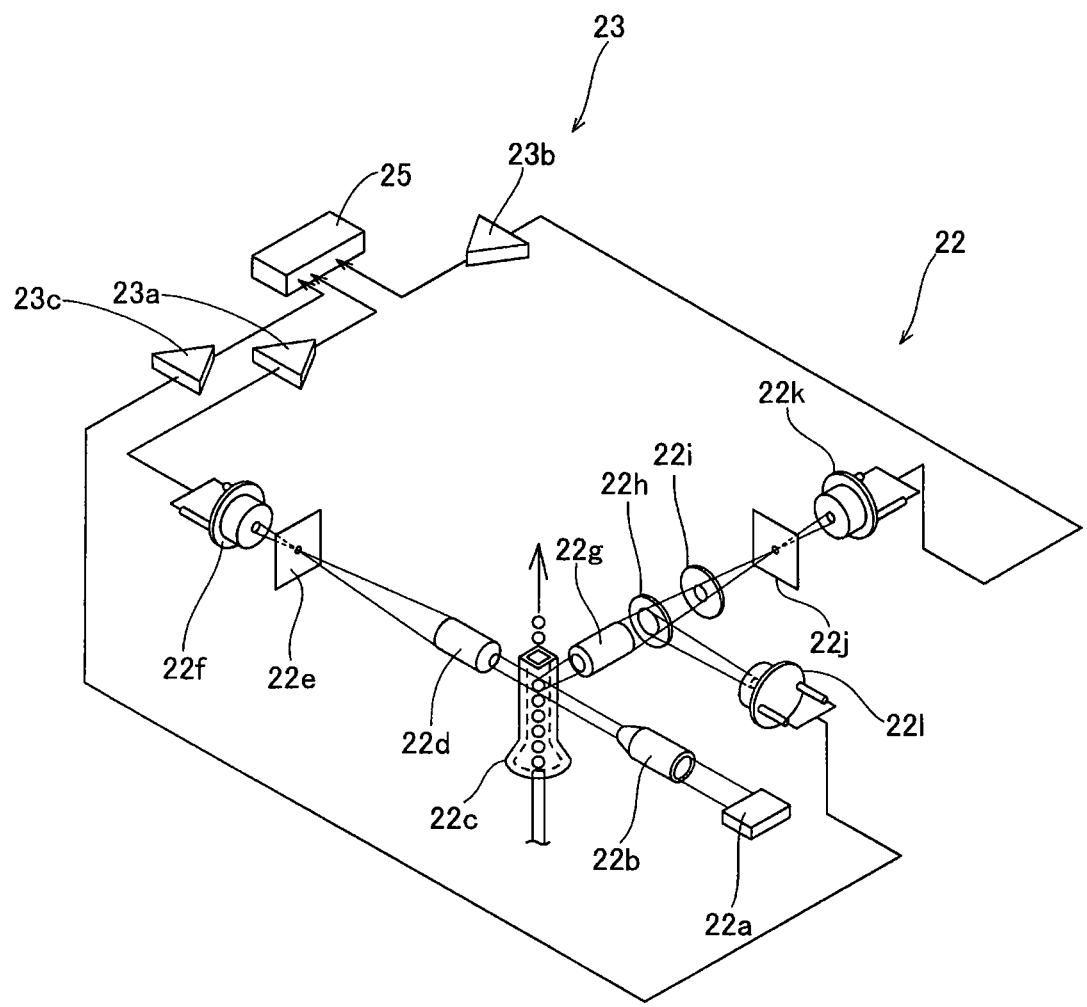
FIG. 4 is a schematic view showing a detection unit of the blood specimen processing system including the reagent preparing device according to the first embodiment shown.

As shown in FIG. 4, the detection unit 22 includes a light emitting portion 22a for emitting laser light, an irradiation lens unit 22b, the sheath flow cell 22c irradiated with laser light, a light collecting lens 22d arranged on an extended line in a direction the laser light emitted from the light emitting portion 22a advances, a pin hole 22e and a PD (Photo Diode) 22f, a light collecting lens 22g arranged in a direction intersecting the direction the laser light emitted from the light emitting portion 22a advances, a dichroic mirror 22h, an optical filter 22i, a pin hole 22j and an APD (Avalanche Photo Diode) 22k, and a PD 22l arranged at the side of the dichroic mirror 22h.

The light emitting portion 22a is arranged to emit light to the sample flow including the measurement sample that passes the inside of the sheath flow cell 22c. The irradiation lens unit 22b is arranged to convert the light emitted from the light emitting portion 22a to parallel light. The PD 22f is arranged to receive the forward scattered light output from the sheath flow cell 22c. The information on the size of the particle (blood cell) in the measurement sample can be obtained from the forward scattered light output from the sheath flow cell 22c.

The dichroic mirror 22h is arranged to separate the lateral scattered light and the lateral fluorescence output from the sheath flow cell 22c. Specifically, the dichroic mirror 22h is arranged to have the lateral scattered light output from the sheath flow cell 22c enter to the PD 22l, and to have the lateral fluorescence output from the sheath flow cell 22c enter to the APD 22k. The PD 22l is arranged to receive the lateral scattered light. Internal information, for example, the size of the core of the particle (blood cell) in the measurement sample can be obtained from the lateral scattered light output from the sheath flow cell 22c. The APD 22k is arranged to receive the lateral fluorescence. Information on the staining degree of the particle (blood cell) in the measurement sample can be obtained from the lateral fluorescence output from the sheath flow cell 22c. The PD 22f, 22l, and the APD 22k respectively have a function of converting the received optical signal to an electrical signal.

As shown in FIG. 4, the analog processing unit 23 includes amplifiers 23a, 23b, and 23c. The amplifiers 23a, 23b, and 23c are respectively arranged to perform amplification and waveform processing on the electrical signal output from the PD 22f, 22l, and the APD 22k.

As shown in FIG. 2, the microcomputer 25 includes a control portion 251 including a control processor and a memory for operating the control processor, an A/D converter 252 for converting a signal output from the analog processing unit 23 to a digital signal, and a calculating portion 253 for performing a predetermined process on the digital signal output from the A/D converter 252.

The control portion 251 has a function of controlling the measurement sample preparing unit 21 and the detection unit 22 through a bus 254a and an interface 255a. The control portion 251 is connected with the display/operation unit 24 through the bus 254a and an interface 255b, and connected with the data processing section 3 through a bus 254b and an interface 255c. The calculating portion 253 has a function of outputting a calculation result to the control portion 251 through an interface 255d and the bus 254a. The control portion 251 has a function of transmitting the calculation result (measurement data) to the data processing section 3.

Figure 5:
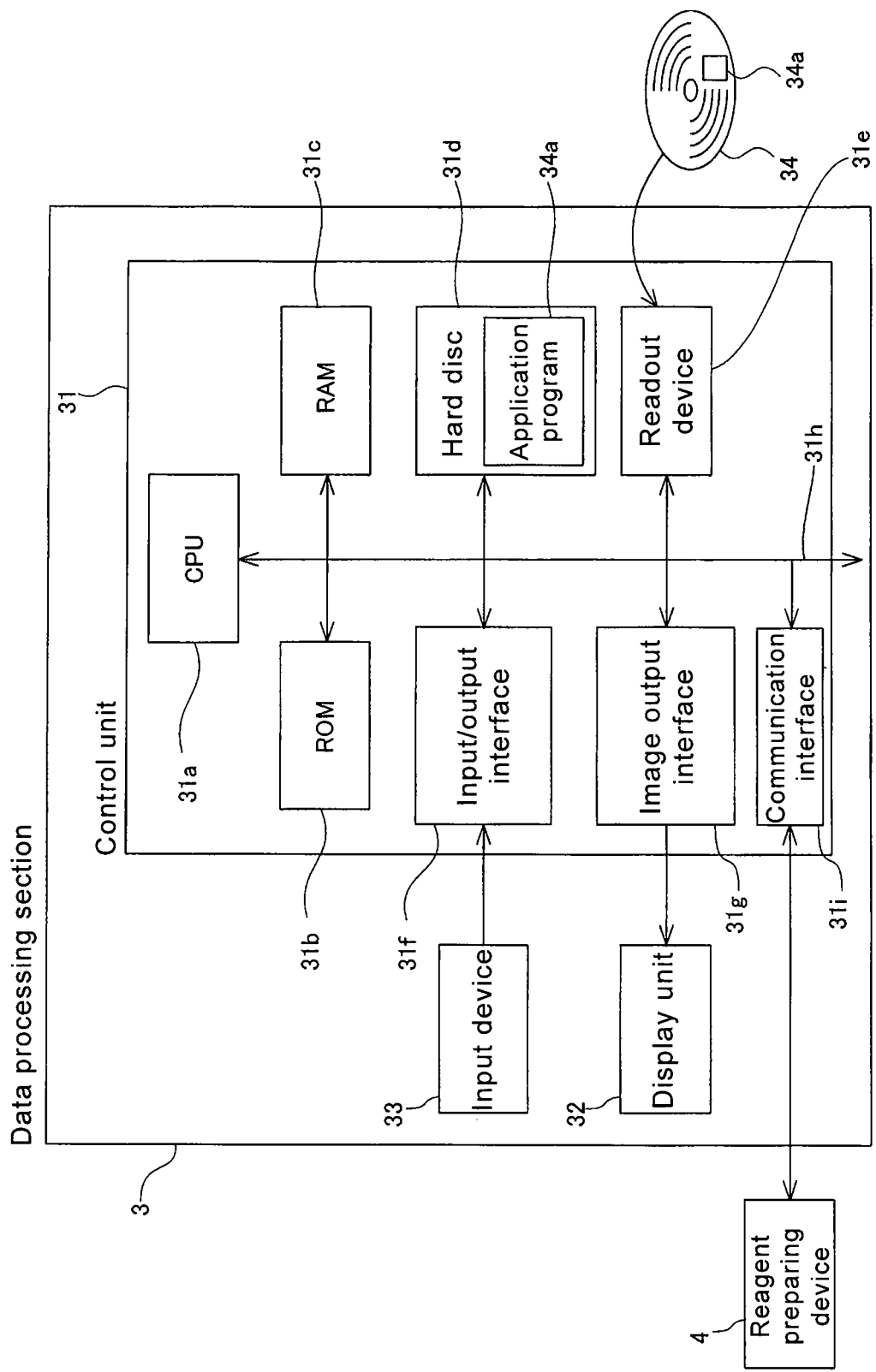
FIG. 5 is a block diagram showing a configuration of a data processing section of the blood specimen processing system including the reagent preparing device according to the first embodiment.

As shown in FIG. 1, the data processing section 3 includes a personal computer (PC) and the like, and has a function of analyzing the measurement data of the measurement section 2 and displaying the analysis result. The data processing section 3 includes a control unit 31, a display unit 32, and an input device 33, as shown in FIG. 5.

The control unit 31 has a function of transmitting a measurement start signal including the measurement mode information and a shutdown signal to the measurement section 2. As shown in FIG. 5, the control unit 31 is also configured by a CPU 31a, a ROM 31b, a RAM 31c, a hard disc 31d, a readout device 31e, an input/output interface 31f, an image output interface 31g and a communication interface 31i. The CPU 31a, the ROM 31b, the RAM 31c, the hard disc 31d, the readout device 31e, the input/output interface 31f, the image output interface 31g and the communication interface 31i are connected by a bus 31h.

The CPU 31a is arranged to execute computer programs stored in the ROM 31b and the computer programs loaded in the RAM 31c. The ROM 31b is configured by mask ROM, PROM, EPROM, EEPROM, and the like, and is recorded with computer programs to be executed by the CPU 31a, data used for the same, and the like.

The RAM 31c is configured by SRAM, DRAM and the like. The RAM 31c is used to read out the computer programs recorded on the ROM 31b and the hard disc 31d. The RAM 31c is used as a work region of the CPU 31a when executing the computer programs.

The hard disc 31d is installed with various computer programs to be executed by the CPU 31a such as operating system and application program, as well as data used in executing the computer program. The application program 34a described later is also installed in the hard disc 31d.

The readout device 31e is configured by flexible disc drive, CD-ROM drive, DVD-ROM drive and the like, and is able to read out computer programs and data recorded on a portable recording medium 34. The application program 34a causing the computer to implement a predetermined function is stored in the portable recording medium 34. The computer serving as the data processing section 3 reads out the application program 34a from the portable recording medium 34, and installs the application program 34a to the hard disc 31d. The application program 34a includes an analyzing program for analyzing the specimen measured in the measurement section, and outputting the analysis result as an analysis result of the specimen. The application program 34a also includes software having a function serving as a clock, and the analyzing program outputs the analysis result with the measurement time of the specimen corresponded to the analysis result.

The application program 34a is not only provided by the portable recording medium 34, and may be provided through an electrical communication line (wired or wireless) from external devices communicably connected with the data processing section 3 by the electrical communication line. For instance, the application program 34a may be stored in the hard disc of the server computer on the Internet, wherein the data processing section 3 can access the server computer to download the application program 34a and install the application program 34a in the hard disc 31d.

Operating system providing graphical user interface environment such as WINDOWS® manufactured and sold by US Microsoft Co. is installed in the hard disc 31d. In the following description, the application program 34a according to the first embodiment is assumed to be operating on the operating system.

The input/output interface 31f is configured by serial interface such as USB, IEEE1394 and RS-232C; parallel interface such as SCSI, IDE and IEEE 1284; analog interface such as a D/A converter and an A/D converter, and the like. The input device 33 including a keyboard and a mouse is connected to the input/output interface 31f, so that the user can input data to the data processing section 3 using the input device 33. The user can also select the measurement mode, and activate and shut down the measurement section 2 using the input device 33.

The image output interface 31g is connected to the display unit 32 configured by LCD, CRT or the like, and is configured to output a video signal corresponding to the image data provided from the CPU 31a to the display unit 32. The display unit 32 displays the image (screen) according to the input video signal.

The reagent preparing device 4 is arranged to prepare the reagent to use in a measurement sample preparing unit 21 of the measurement section 2. Specifically, the reagent preparing device 4 is configured to prepare the reagent to use for blood analysis by diluting the high concentration reagent to a desired concentration using the RO water produced by the RO water producing unit 7 arranged at the exterior. The RO water is one type of pure water and is water in which impurities are removed by being transmitted through an RO (Reverse Osmosis) membrane (reverse osmosis membrane). Other than the RO water, the pure water includes purified water, deionized water and distilled water, and is water subjected to the process of removing impurities, and the purity is not particularly limited. The high concentration reagent is an undiluted solution of the reagent, and has higher concentration of the contained component than the reagent supplied to the measurement section 2.

Figure 6:
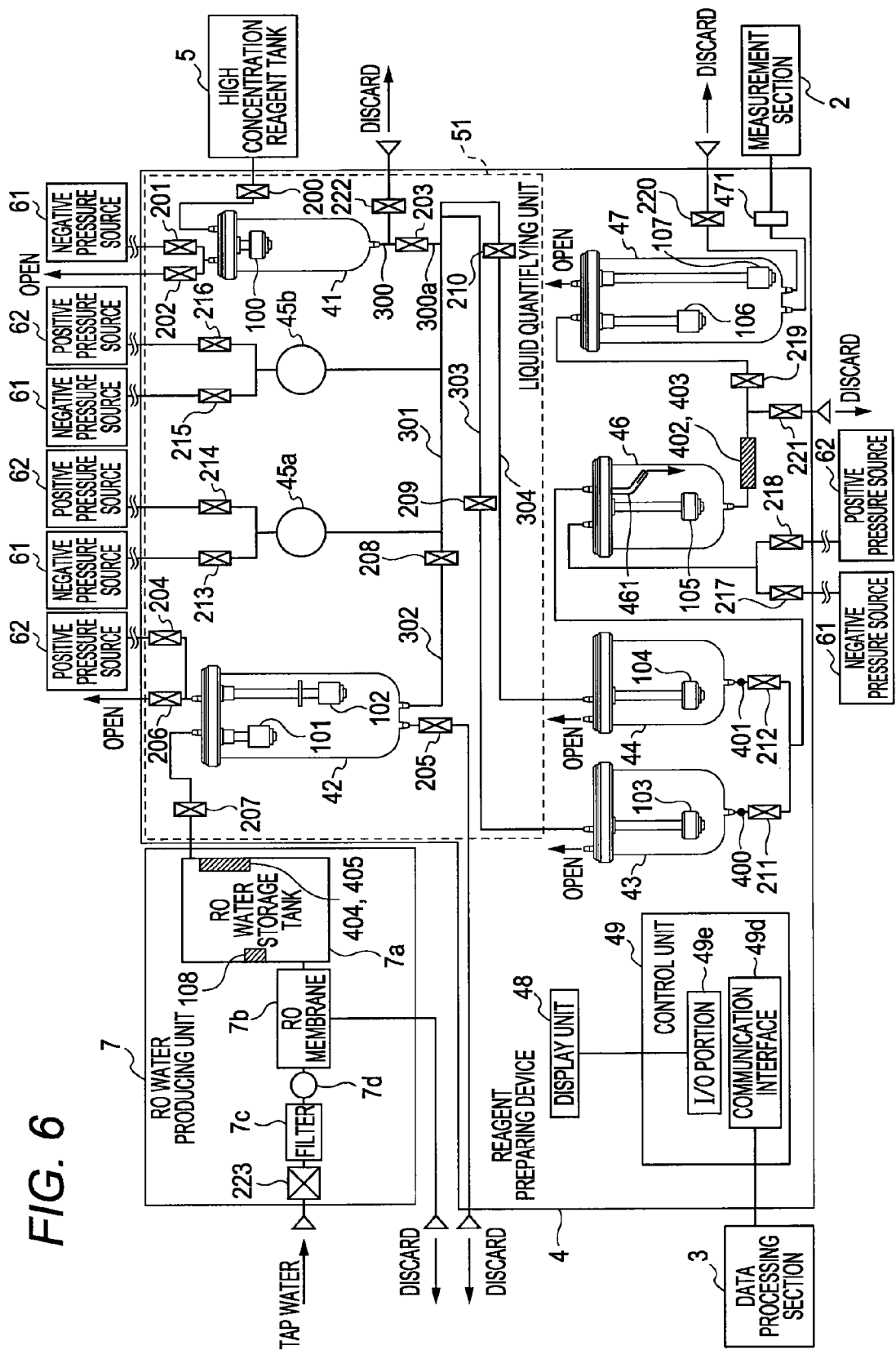
FIG. 6 is a block diagram showing a configuration of the reagent preparing device according to the first embodiment shown.

As shown in FIG. 6, the reagent preparing device 4 includes a high concentration reagent chamber 41, a RO water chamber 42, two diluting chambers 43 and 44, two diaphragm pumps 45a and 45b, a stirring chamber 46, a supply chamber 47, a display unit 48, a control unit 49 for controlling each unit of the reagent preparing device 4, and a barcode reader 50 (see FIG. 1). The reagent preparing device 4 also includes a pneumatic unit 6 (see FIG. 1) installed at the exterior of the housing, and is configured to send each liquid in the device using negative pressure and positive pressure supplied from the pneumatic unit 6. The pneumatic unit 6 includes a negative pressure source 61 for supplying negative pressure and a positive pressure source 62 for supplying positive pressure to the reagent preparing device 4.

The high concentration reagent chamber 41 is configured to supply the high concentration reagent from a high concentration reagent tank 5. The high concentration reagent chamber 41 includes a float switch 100 for detecting that a predetermined amount of high concentration reagent is stored in the chamber. The float switch 100 is configured such that the float portion moves up and down according to the liquid amount (liquid level) in the high concentration reagent chamber 41. Each unit is controlled by the control unit 49 such that the high concentration reagent is supplied from the high concentration reagent tank 5 to the high concentration reagent chamber 41 when the float portion of the float switch 100 reaches the lower limit. Furthermore, each unit is controlled by the control unit 49 such that the supply of the high concentration reagent from the high concentration reagent tank 5 to the high concentration reagent chamber 41 is stopped when the float portion of the float switch 100 reaches the upper limit. The float switch 100 is arranged near the upper end of the high concentration reagent chamber 41, and is configured such that the float portion reaches the upper limit when about 300 mL of the high concentration reagent is stored in the high concentration reagent chamber 41. The high concentration reagent is thus supplied such that about 300 mL is stored in the high concentration reagent chamber 41 on a constant basis.

The high concentration reagent chamber 41 is connected to the high concentration reagent tank 5 through an electromagnetic valve 200, and is connected to the negative pressure source 61 of the pneumatic unit 6 through an electromagnetic valve 201. The high concentration reagent chamber 41 is also configured to be opened to atmosphere or closed by the opening and closing of the electromagnetic valve 202. The high concentration reagent chamber 41 is connected to a flow path 301 for transferring the liquid from the diaphragm pump 45a (45b) to the diluting chamber 43 (44) by the flow path 300. An electromagnetic valve 203 is arranged on the flow path 300, which electromagnetic valve 203 is arranged near the flow path 301. Specifically, the length of the flow path 300a between the electromagnetic valve 203 and the flow path 301 is set to a small length of about 15 mm. The flow path 300 (300a) connected to the high concentration reagent chamber 41 has an inner diameter of about 1.8 mm, and the flow path 301 has an inner diameter of about 4.0 mm.

The high concentration reagent chamber 41 is configured to discard the high concentration reagent in the chamber. Specifically, the high concentration reagent 41 is connected to a discard flow path through an electromagnetic valve 222, so that the high concentration reagent inside is discharged to the discard flow path by opening the electromagnetic valves 202 and 222. The discard flow path of the high concentration reagent is branched from the flow path 300.

The RO water chamber 42 is configured such that the RO water for diluting the high concentration reagent is supplied from the RO water producing unit 7.

The RO water chamber 42 includes float switches 101 and 102 for detecting that the RO water stored in the chamber has reached the upper limit amount and the lower limit amount, respectively. The float switch 101 (102) is configured such that the float portion moves up and down according to the liquid amount (liquid level) in the RO water chamber 42. Each unit is controlled by the control unit 49 such that the supply of RO water from the RO water producing unit 7 to the RO water chamber 42 is stopped when the float portion of the float switch 101 reaches the position corresponding to the upper limit amount. Furthermore, each unit is controlled by the control unit 49 such that the RO water is supplied from the RO water producing unit 7 to the RO water chamber 42 when the float portion of the float switch 102 reaches the position corresponding to the lower limit amount.

The float switch 101 is arranged near the upper end of the RO water chamber 42, and is configured such that the float portion reaches the position corresponding to the upper limit amount of the RO water chamber 42 when about 600 mL of the RO water is stored in the RO water chamber 42. The float switch 102 is configured such that the float portion reaches the position corresponding to the lower limit amount of the RO water chamber 42 when the RO water stored in the RO water chamber 42 reduces to about 300 mL. The RO water of greater than or equal to about 300 mL and less than or equal to about 600 mL is thus stored in the RO water chamber 42 while the reagent preparing device 4 is operating.

The RO water chamber 42 is configured so that the RO water in the chamber can be discarded. Specifically, the RO water chamber 42 is connected to the positive pressure source 62 through the electromagnetic valve 204 and connected to a discard flow path through the electromagnetic valve 205, so that the RO water inside is pushed out to the discard flow path by the positive pressure force by opening both electromagnetic valves 204 and 205. The RO water chamber 42 is configured to be opened to atmosphere and closed by the opening and closing of the electromagnetic valve 206. The RO water chamber 42 is connected to the RO water storage tank 7a, to be hereinafter described, of the RO water producing unit 7 through the electromagnetic valve 207. The RO water chamber 42 is connected to the diaphragm pumps 45a and 45b by the flow path 302 through the electromagnetic valve 208.

The diluting chambers 43 and 44 are respectively arranged to dilute the high concentration reagent with the RO water. As hereinafter described, the diluting chamber 43 (44) is configured to store about 300 mL of liquid (mixed solution of high concentration reagent and RO water) sent by the diaphragm pumps 45a and 45b. The diluting chamber 43 (44) includes a float switch 103 (104) for detecting that the remaining amount of the liquid (mixed solution of high concentration reagent and RO water) stored in the chamber has reached a predetermined amount. The float switch 103 (104) is configured such that the float portion moves up and down according to the liquid amount (liquid level) in the diluting chamber 43 (44). The diluting chamber 43 (44) is configured so as to be always opened to atmosphere.

The diluting chamber 43 (44) is connected to the flow path 301 by the flow path 303 (304) through the electromagnetic valve 209 (210). The flow path 303 (304) has an inner diameter of about 4 mm, similar to the flow path 301. The liquid (RO water and high concentration reagent) transferred through the flow path 301 can be transferred to the diluting chamber 43 by opening the electromagnetic valve 209 with the electromagnetic valve 210 closed. The liquid (RO water and high concentration reagent) transferred through the flow path 301 can be transferred to the diluting chamber 44 by opening the electromagnetic valve 210 with the electromagnetic valve 209 closed. In other words, the electromagnetic valves 209 and 210 are respectively configured to function as a flow path switching unit of the flow paths 303 and 304.

The diluting chamber 43 (44) is connected to the stirring chamber 46 through the electromagnetic valve 211 (212). An air bubble sensor 400 (401) is arranged between the diluting chamber 43 (44) and the electromagnetic valve 211 (212). The air bubble sensor 400 (401) is a transmissive sensor, and is configured to detect air bubbles that pass the flow path. That the liquid (mixed solution of high concentration reagent and RO water) in the diluting chamber 43 (44) are all discharged can be checked by the control unit 49 when the float portion of the float switch 103 (104) reaches the lower limit and the air bubbles are detected by the air bubble sensor 400 (401). When the diluting chamber 43 (44) becomes empty (all liquid in the chamber is discharged), each unit is controlled by the control unit 49 so that the high concentration reagent and the RO water are supplied to the empty diluting chamber 43 (44).

The diaphragm pumps 45a and 45b have similar configuration with respect to each other, and are configured to perform the same operation at the same time. The diaphragm pump 45a (45b) has a function of quantifying the liquid (high concentration reagent or RO water) by about 6 mL (total of about 12 mL with two pumps) (constant amount) in one quantifying operation. The diaphragm pump 45a (45b) is connected to the negative pressure source 61 through the electromagnetic valve 213 (215), and also connected to the positive pressure source 62 through the electromagnetic valve 214 (216). The high concentration reagent chamber 41, the RO water chamber 42, the diaphragm pumps 45a and 45b, the pneumatic unit, the flow paths 300 to 304, and the electromagnetic valves 200 to 210 and 213 to 216 configure a liquid quantifying unit 51 (see FIG. 6) of the reagent preparing device 4.

As shown in FIG. 6, the stirring chamber 46 is configured to accommodate about 300 mL of liquid, and is arranged to stir the liquid (mixed solution of high concentration reagent and RO water) transferred from the diluting chamber 43 (44). Specifically, the stirring chamber 46 includes a bent pipe 461, and is configured so that the liquid (mixed solution of high concentration reagent and RO water) transferred from the diluting chamber 43 (44) flows into the stirring chamber 46 along the inner wall surface of the stirring chamber 46 by passing the pipe 461. The liquid (mixed solution of high concentration reagent and RO water) transferred from the diluting chamber 43 (44) thus flows along the inner wall surface of the stirring chamber 46, whereby convention occurs and the high concentration reagent and the RO water are easily stirred. The high concentration reagent and the RO water are stirred to a certain extent in the diluting chamber 43 (44) and in the flow path from the diluting chamber 43 (44) to the stirring chamber 46, but the solution is more reliably stirred by configuring the stirring chamber 46 in the above manner.

The stirring chamber 46 includes a float switch 105 for detecting that the remaining amount of the liquid (mixed solution of high concentration reagent and RO water) accommodated in the chamber has reached a predetermined amount. The float switch 105 is configured such that the float portion moves up and down according to the liquid amount (liquid level) in the stirring chamber 46. Each unit is controlled by the control unit 49 such that about 300 mL of mixed solution is supplied from either diluting chamber 43 or 44 to the stirring chamber 46 when the float portion of the float switch 105 reaches the lower limit and the interior of the chamber becomes empty. When the mixed solution supplied from either diluting chamber 43 or 44 and stirred is discharged from the stirring chamber 46, about 300 mL of mixed solution is then supplied from the other diluting chamber 43 or 44 to the stirring chamber 46. The stirring chamber 46 is connected to the negative pressure source 61 through the electromagnetic valve 217, and connected to the positive pressure source 62 through the electromagnetic valve 218.

The supply chamber 47 is arranged to store a predetermined amount of reagent to supply to the measurement section 2. The supply chamber 47 has an accommodation amount of about 600 mL. The supply chamber 47 includes a float switch 106 for detecting that the remaining amount of reagent stored in the chamber has reached about 300 mL. The supply chamber 47 also includes a float switch 107 for detecting that the remaining amount of reagent stored in the supply chamber 47 is substantially zero. The float switch 106 (107) is configured such that the float portion moves up and down according to the liquid amount (liquid level) in the supply chamber 47. The float portion of the float switch 106 is configured to be movable from the vicinity of the upper end in the height direction of the supply chamber 47 to the intermediate position. Each unit is controlled by the control unit 49 so that about 300 mL of reagent of the desired concentration is supplied from the stirring chamber 46 to the supply chamber 47 when the float portion of the float switch 106 reaches the intermediate position in the height direction of the supply chamber 47 (lower limit position in the movable range of the float portion of the float switch 106). The reagent of desired concentration of greater than or equal to about 300 mL and less than or equal to about 600 mL is stored in the supply chamber 47 on a constant basis. The reagent can be rapidly supplied to the measurement section 2 according to the supply instruction by storing a predetermined amount of reagent in the supply chamber 47.

The float portion of the float switch 107 is configured to be movable to the vicinity of the bottom of the supply chamber 47. The supply of reagent to the measurement section 2 is stopped when detected that the remaining amount of reagent accommodated in the chamber is substantially zero by the float switch 107. Therefore, the air bubbles are prevented from mixing to the reagent to be supplied to the measurement section 2 while continuing the supply of reagent to the measurement section 2 as much as possible even if the reagent is not transferred to the supply chamber 47 for some reasons.

The supply chamber 47 is connected to the stirring chamber 46 through the electromagnetic valve 219. The supply chamber 47 is configured so that the reagent in the chamber can be discarded at the time of maintenance and the like by opening the electromagnetic valve 220. The supply chamber 47 is configured so as to be opened to atmosphere on a constant basis. The supply chamber 47 is connected to the measurement section 2 through the filter 471. The filter 471 is arranged to prevent impurities from mixing in the reagent to be supplied to the measurement section 2.

A conductivity sensor 402 for measuring the electrical conductivity of the reagent is arranged between the stirring chamber 46 and the supply chamber 47. The conductivity sensor 402 includes a temperature sensor 403 for measuring the temperature of the reagent at the position where the conductivity sensor 402 is arranged. A discard flow path is connected between the conductivity sensor 402 and the electromagnetic valve 219 through the electromagnetic valve 221.

As shown in FIG. 1, the display unit 48 is arranged on the outer surface of the reagent preparing device 4. The display unit 48 is configured by a touch panel liquid crystal display.

Figure 7:
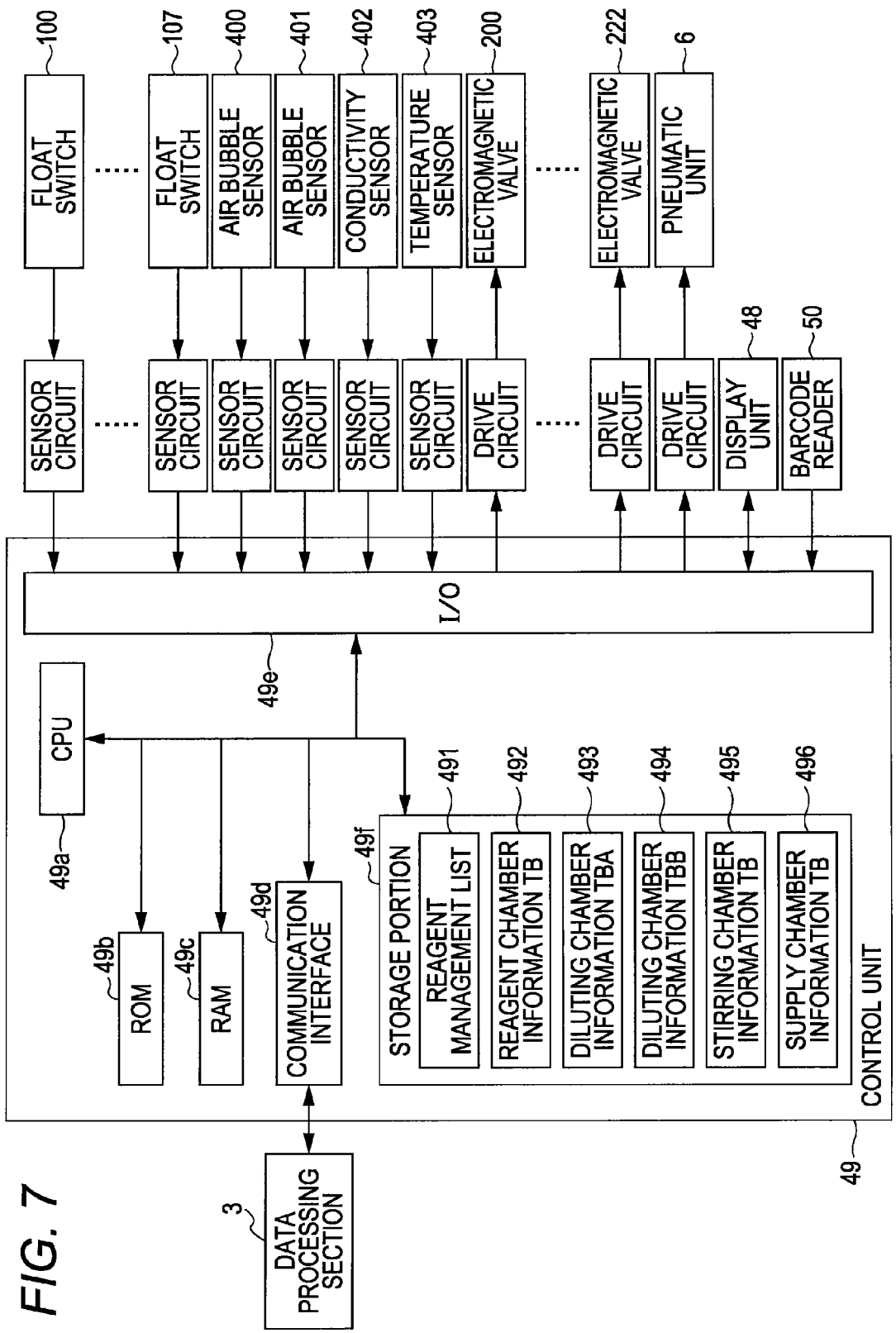
FIG. 7 is a block diagram explaining a control unit of the reagent preparing device according to the first embodiment of the present invention.
Figure 8:
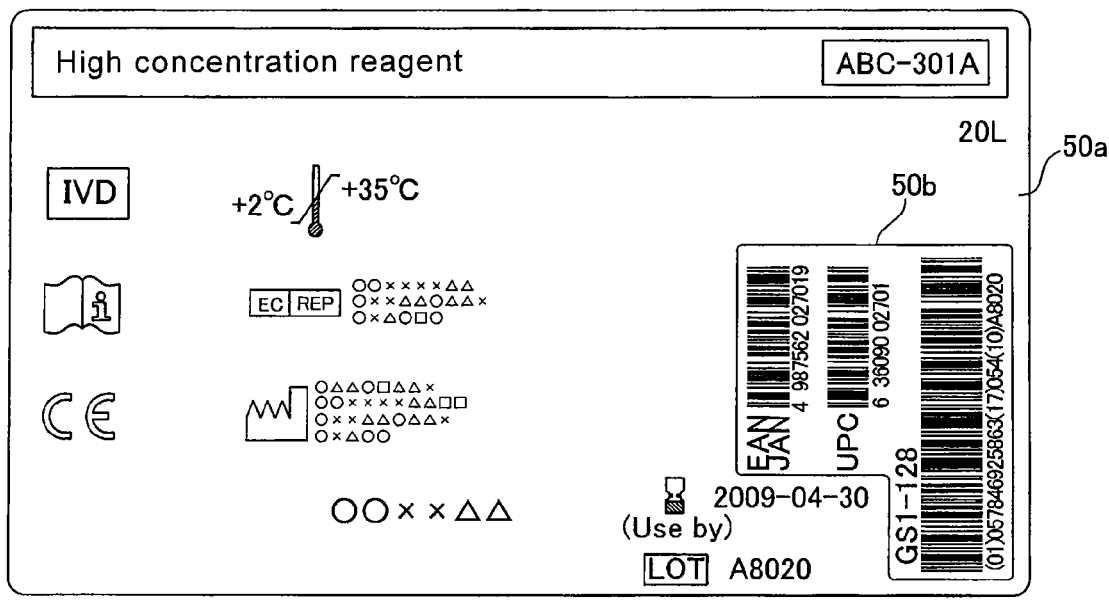
FIG. 8 is a view describing a barcode reader of the reagent preparing device according to the first embodiment of the present invention.

As shown in FIG. 7, the control unit 49 includes a CPU 49a, a ROM 49b, a RAM 49c, a communication interface 49d connected to the data processing section 3, an I/O (Input/Output) portion 49e connected to each unit in the reagent preparing device 4, and a storage portion 49f.

The CPU 49a can execute computer programs stored in the ROM 49b and the computer programs loaded in the RAM 49c. The CPU 49a is configured to use the RAM 49c as a work region when executing the computer programs. One of such computer programs is software having a function serving as a clock. The current time by the software of the reagent preparing device 4 and the current time by the software of the data processing section 3 are preferably matched.

A general formula for obtaining a target value of the electrical conductivity of the reagent is expressed with the following equation (1).

$$Z_0 = \{X + (A-1)Y\}/A \quad (1)$$

In the equation (1), $Z_0$ is, at 25° C., the target value (ms/cm) of the electrical conductivity of the reagent in which the high concentration reagent and the RO water are mixed and stirred, X is the electrical conductivity (ms/cm) of the high concentration reagent at 25° C., Y is the electrical conductivity (ms/cm) of the RO water at 25° C., and A is the diluting magnification (known) (25 times in the first embodiment). Here, X is a value unique to the high concentration reagent, and is a known value obtained through experiments and the like in advance.

The correction formula for taking into consideration the temperature of the RO water obtained by the temperature sensor 405 and the temperature of the reagent obtained by the temperature sensor 403 is expressed with the following equation (2).

$$Z = [\{X + (A-1)Y\}/A] \times \{1 + \alpha1(T2-25)\} = [[X + (A-1)Y1/\{1 + \alpha0(T1-25)\}]/A] \times \{1 + \alpha1(T2-25)\} \quad (2)$$

In the equation (2), Z is, at T2° C., the target value (ms/cm) of the electrical conductivity of the reagent in which the high concentration reagent and the RO water are mixed and stirred, Y1 is the electrical conductivity of the RO water at T1° C., T1 is the temperature of the RO water (° C.), T2 is the temperature (° C.) of the reagent in which the high concentration reagent and the RO water are mixed and stirred, $\alpha0$ is the temperature coefficient compared with the electrical conductivity of the RO water at 25° C., and $\alpha1$ is the temperature coefficient compared with the electrical conductivity of the reagent in which the high concentration reagent and the RO water are mixed and stirred, at 25° C. The temperature coefficients $\alpha0$ and $\alpha1$ differ depending on the type and concentration of the liquid, but are 0.02 for simplification in JIS (Japanese Industrial Standards).

The CPU 49a is configured to calculate the target value Z from equation (2). Therefore, the CPU 49a determines the target value based on the desired diluting magnification A (known), the detection value Y1 of the electrical conductivity of the RO water, the measurement value T1 of the temperature of the RO water, the measurement value T2 of the temperature of the mixed and stirred reagent, and the electrical conductivity X (known) of the high concentration reagent.

In the first embodiment, the CPU 49a is configured to store the high concentration reagent information such as the lot number, the pre-opening expiration date, the use start date, the post-opening expiration date, and the like of the high concentration reagent in the storage portion 49f. Specifically, as hereinafter described, a reagent management list 491 is stored in the storage portion 49f, and the CPU 49a records the high concentration reagent information in the reagent management list 491 based on the read information by the barcode reader 50.

The CPU 49a is configured to update a reagent chamber information table 492, to be described later, stored in the storage portion 49f when about 300 mL of high concentration reagent or the accommodation upper limit amount of the high concentration reagent chamber 41 is aspirated from the high concentration chamber 41 to the diaphragm pump 45a (45b) after acquiring the high concentration reagent information. The CPU 49a is also configured to update a diluting chamber information table A493 and a diluting chamber information table B494, to be hereinafter described, of the storage portion 49f when about 300 mL of mixed solution of the high concentration reagent and the RO water is transferred to the diluting chambers 43 and 44. The CPU 49a is also configured to update a stirring chamber information table 495, to be hereinafter described, of the storage portion 49f when about 300 mL of mixed solution of the high concentration reagent and the RO water is transferred from the diluting chamber 43 (44) to the stirring chamber 46, and to update a supply chamber information table 496, to be hereinafter described, of the storage portion 49f when about 300 mL of mixed solution (prepared reagent) is transferred from the stirring chamber 46 to the supply chamber 47.

The CPU 49a is configured to accept an activation instruction and a shutdown instruction of the reagent preparing device 4 from the user through the display unit 48 of a touch panel type.

The communication interface 49d is configured to transmit error information to the data processing section 3 so that the user can check the error that occurred in the reagent preparing device 4. The error information includes information for urging replacement of the high concentration reagent tank 5, information notifying that the RO water is no longer supplied, and information notifying the abnormality of the negative pressure source 61 and the positive pressure source 62.

As shown in FIG. 7, the I/O portion 49e is configured to receive signals from the float switches 100 to 107, the air bubble sensors 400, 401, the conductivity sensor 402, and the temperature sensor 403 through each sensor circuit. The I/O portion 49e is configured to output signals to each drive circuit to control the drive of the electromagnetic valves 200 to 222 and the pneumatic unit 6 through each drive circuit.

The I/O portion 49e is configured to receive the signal corresponding to the instruction of the user from the display unit 48 of the touch panel type and to output a video signal such as image data to the display unit 48. The I/O portion 49e is configured to receive information related to the high concentration reagent read by the barcode reader 50.

The storage portion 49f includes a non-volatile memory, and stores the reagent management list 491, the reagent chamber information table 492 containing information on the high concentration reagent in the high concentration reagent chamber 41, the diluting chamber information table A493 containing information on the high concentration reagent in the diluting chamber 43, the diluting chamber information table B494 containing information on the high concentration reagent in the diluting chamber 44, the stirring chamber information table 495 containing information on the high concentration reagent in the stirring chamber 46, and the supply chamber information table 496 containing information on the high concentration reagent in the supply chamber 47.

The reagent management list 491 is configured to be rewritable by the CPU 49a, and can record a maximum of 100 high concentration reagent information. If the high concentration reagent information exceeds 100, the high concentration reagent information is sequentially overwritten from the oldest information. The reagent chamber information table 492, the diluting chamber information table A493, the diluting chamber information table B494, the stirring chamber information table 495, and the supply chamber information table 496 are configured to be rewritable by the CPU 49a, and are configured to be updated to new information at a predetermined timing, as hereinafter described. The reagent chamber information table 492, the diluting chamber information table A493, the diluting chamber information table B494, and the stirring chamber information table 495 each contain the pre-opening expiration date information of the high concentration reagent accommodated in each chamber, and the post-opening expiration date information of the high concentration reagent.

The supply chamber information table 496 contains the flow-in time information to the supply chamber 47 in addition to the pre-opening expiration date information of the high concentration reagent accommodated in the chamber and the post-opening expiration date information of the high concentration reagent. In the first embodiment, the flow-in time to the supply chamber 47 is the time the prepared reagent passes the conductivity sensor 402 when being transferred from the stirring chamber 46 to the supply chamber 47. Since the reagents prepared at different times are simultaneously accommodated in the supply chamber 47, as hereinafter described, different high concentration reagent (high concentration reagent having different high concentration reagent information) coexist. Specifically, the reagent newly transferred to the supply chamber 47 mixes with the reagent remaining in the supply chamber 47 since the new reagent is supplied when the remaining amount of the reagent in the supply chamber 47 becomes about 300 mL.

After the reagent A is transferred to the supply chamber 47, one part of the reagent A remains in the supply chamber 47 with the reagent B to be newly transferred the next to the supply chamber 47 even if about 300 mL of reagent in the supply chamber 47 is transferred from the supply chamber 47 to the measurement section 2. Furthermore, even if about 300 mL (total of about 600 mL after reagent A is transferred to the supply chamber 47) of reagent in the supply chamber 47 is transferred from the supply chamber 47 to the measurement section 2, one part of the reagent A is assumed to remain in the supply chamber 47 with the reagent B and the new reagent C. Furthermore, by the time about 300 mL (total of about 900 mL after reagent A is transferred to the supply chamber 47) of reagent in the supply chamber 47 is transferred from the supply chamber 47 to the measurement section 2, almost all the reagent A is assumed to be transferred from the supply chamber 47 to the measurement section 2. In other words, the reagent A is assumed to be not remaining in the supply chamber 47 by the time the fourth reagent D, counting from reagent A, is transferred to the supply chamber 47. Thus, in the first embodiment, the supply chamber information table 496 can record the pre-opening expiration date information, the post-opening expiration date information, and the flow-in time information of the most recent three reagents (three reagents recently transferred to the supply chamber 47). Thus, the information on the different high concentration reagent having a possibility of being accommodated in the supply chamber 47 can be stored in the supply chamber information table 496.

As shown in FIG. 1, the barcode reader 50 is a handy type and is configured to read a barcode 50b (see FIG. 8) of a label 50a attached to the high concentration reagent tank 5. The barcode 50b contains information unique to each high concentration reagent such as the lot number and the pre-opening expiration date of the high concentration reagent.

The RO water producing unit 7 is configured so that the RO water serving as the diluting liquid for diluting the high concentration reagent can be produced using tap water. The RO water producing unit 7 includes an RO water storage tank 7a, a RO film 7b, and a filter 7c for protecting the RO film 7b by removing impurities contained in the tap water. Furthermore, the RO water producing unit 7 includes a high pressure pump 7d for applying high pressure to the water passed through the filter 7c so that water molecules transmit through the RO film 7b, and an electromagnetic valve 223 for controlling the supply of tap water.

The RO water storage tank 7a is arranged to store the RO water transmitted through the RO film 7b. The RO water storage tank 7a includes a float switch 108 for detecting that a predetermined amount of RO water is stored. The RO water storage tank 7a includes a conductivity sensor 404 for measuring the electrical conductivity of the RO water in the RO water storage tank 7a. The conductivity sensor 404 includes a temperature sensor 405 for measuring the temperature of the RO water.

The RO water producing unit 7 is configured to enable to the tap water to reach the filter 7c by opening the electromagnetic valve 222. The RO water producing unit 7 can also transmit the water passed through the filter 7c through the RO film 7b with high pressure by driving the high pressure pump 7d. The RO water producing unit 7 is configured to accommodate a predetermined amount of RO water in the RO water storage tank 7a based on the detection result of the float switch 108. The speed at which the RO water is supplied to the RO water storage tank 7a by the RO water producing unit 7, that is, the production speed of the RO water by the RO water producing unit 7 is greater than or equal to about 20 L/hour and smaller than or equal to about 50 L/hour.

The high concentration reagent information acquisition processing operation of the reagent preparing device 4 according to the first embodiment of the present invention will be described with reference to FIGS. 8 to 11.

Figure 9:
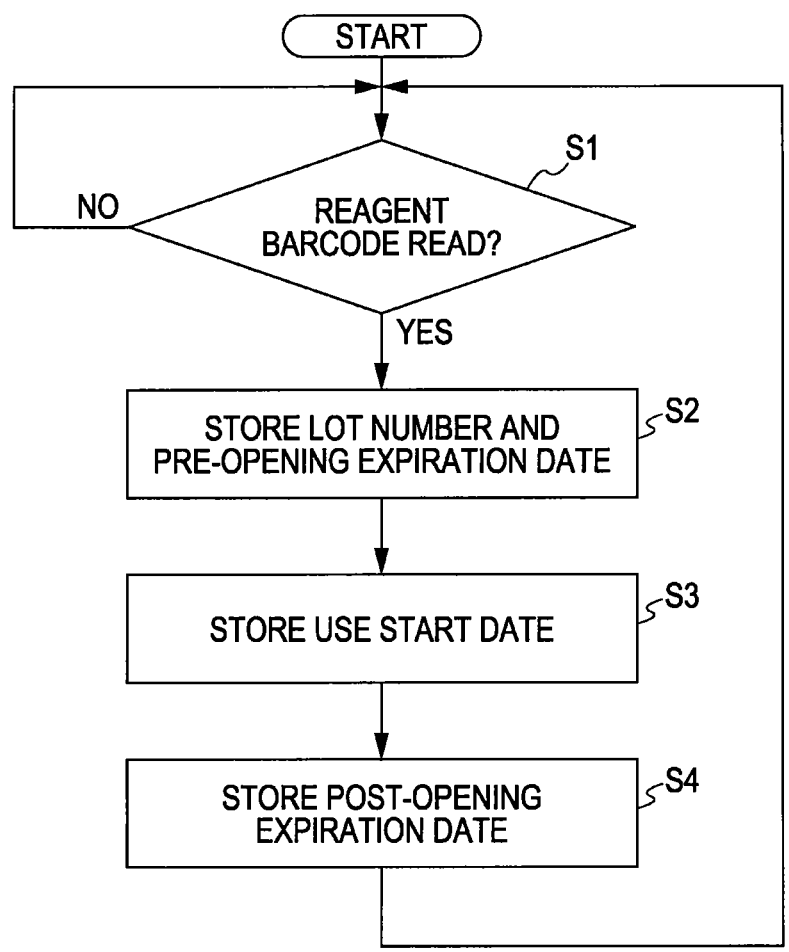
FIG. 9 is a flowchart describing a high concentration reagent information acquisition processing operation of the reagent preparing device according to the first embodiment of the present invention.

First, in step S1 of FIG. 9, whether or not the barcode 50b (see FIG. 8) of the label 50a attached to the high concentration reagent tank 5 is read by the barcode reader 50 is determined by the CPU 49a. Specifically, a reagent replacement screen 482, as shown in FIG. 11, is displayed when a reagent replacement button 481c on a menu screen 481 (see FIG. 10) displayed in the display unit 48 is pushed by the user. Thereafter, the user places the handy type barcode reader 50 on the barcode 50b (see FIG. 8) of the new high concentration reagent tank 5, so that the barcode 50b is read by the barcode reader 50. The barcode 50b shows the lot number, the pre-opening expiration date, and the like of the high concentration reagent tank 5.

Figure 10:
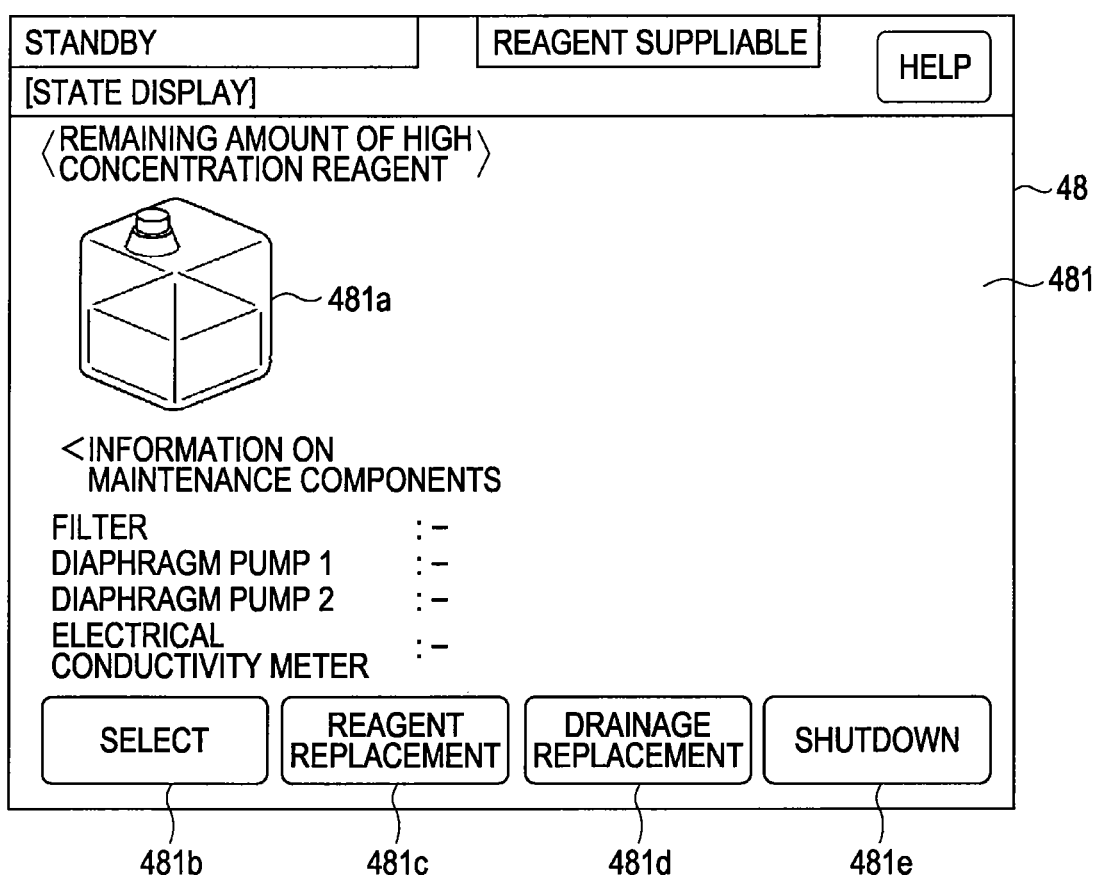
FIG. 10 is a screen view describing the high concentration reagent information acquisition processing operation of the reagent preparing device according to the first embodiment of the present invention.
Figure 11:
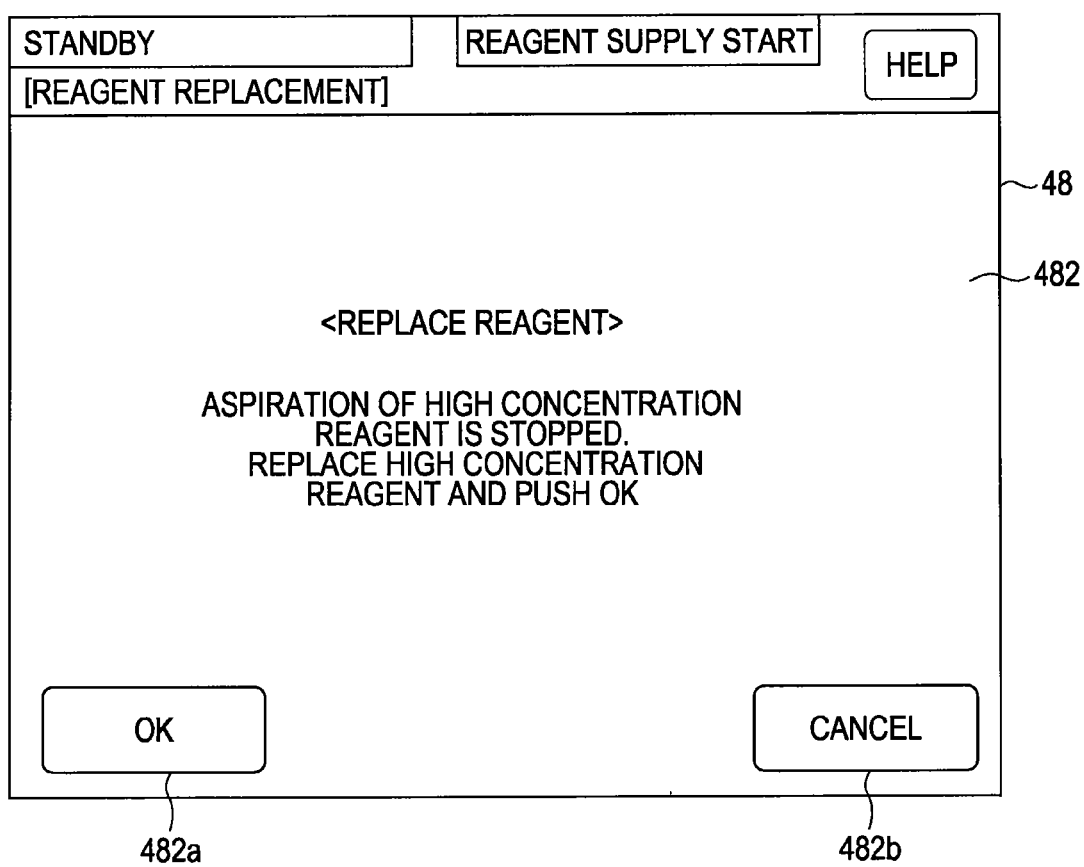
FIG. 11 is a screen view describing the high concentration reagent information acquisition processing operation of the reagent preparing device according to the first embodiment of the present invention.

As shown in FIG. 10, the menu screen 481 displays a schematic view 481a showing the remaining amount of the high concentration reagent, a select button 481b, a reagent replacement button 481c, a drainage replacement button 481d, and a shutdown button 481e. As hereinafter described, the select button 481d is pushed when the user checks various settings and various matters. The drainage replacement button 481d is pushed when replacing a drainage tank (not shown) accommodating the drainage discarded from the reagent preparing device 4. The shutdown button 481e is pushed when shutting down the reagent preparing device 4. The reagent replacement screen 482 displays a notification to stop the aspiration of the high concentration reagent, and a notification to urge the replacement of the high concentration reagent. Furthermore, the reagent replacement screen 482 displays an OK button 482a and a cancel button 482b. The OK button 482a is pushed after the replacement of the high concentration reagent tank 5 is completed. The cancel button 482b is pushed when stopping the replacement of the high concentration reagent tank 5.

In step S1, the above determination is repeated until the barcode 50b is read by the barcode reader 50. After the barcode 50b is read, the lot umber and the pre-opening expiration date of the high concentration reagent are stored in the storage portion 49f based on the barcode 50b by the CPU 49a in step S2. Specifically, the lot number and the pre-opening expiration date of the new high concentration reagent are recorded in the reagent management list 491 of the storage portion 49f.

Thereafter, in step S3, the CPU 49a stores the date the barcode 50b is read in the storage portion 49f as the use start date of the high concentration reagent. In other words, the use start date of the high concentration reagent is recorded in the reagent management list 491 of the storage portion 49f. In step S4, the CPU 49a stores the post-opening expiration date of the high concentration reagent in the storage portion 49f. Specifically, the CPU 49a stores a period of 30 days from the use start date (date the barcode 50b is read) of the high concentration reagent as the post-opening expiration date. In other words, the post-opening expiration date of the high concentration reagent is recorded in the reagent management list 491 of the storage portion 49f. The processes from step S1 to step S4 are repeatedly executed from when the reagent preparing device 4 is activated until shut down.

The reagent preparation processing operation of the reagent preparing device 4 according to the first embodiment of the present invention will now be described with reference to FIGS. 6, 12, and 13.

Figure 12:
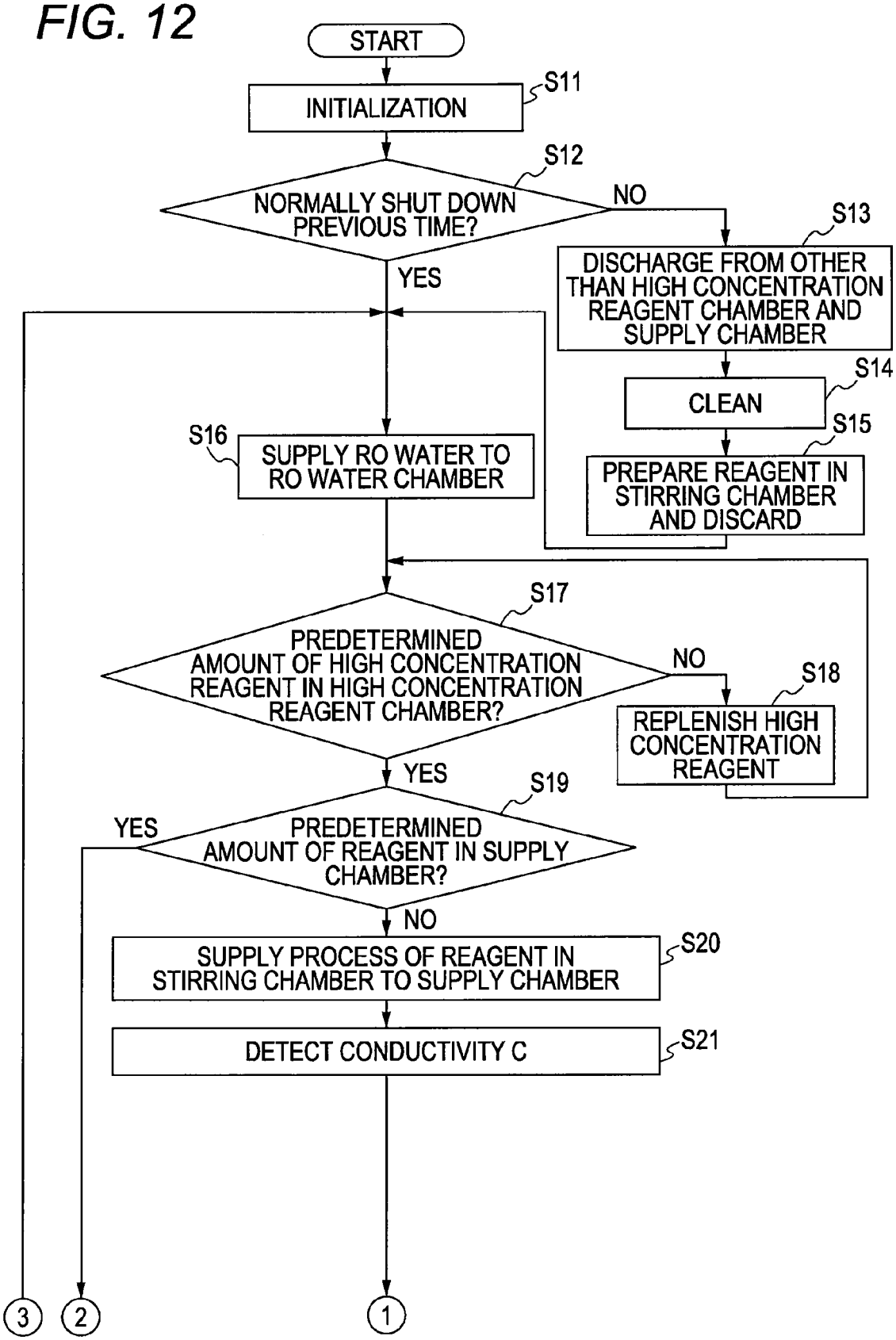
FIG. 12 is a flowchart explaining the reagent preparation processing operation of the reagent preparing device according to the first embodiment of the present invention.

First, in step S11 of FIG. 12, the CPU 49a initializes the computer program stored in the ROM 49b. In step S12, the CPU 49a determines whether or not the reagent preparing device 4 is normally shut down at the end of the previous operation. Specifically, determination is made based on a flag set to ON when normally shut down, as hereinafter described. The process proceeds to step S16 if normally shut down, and the process proceeds to step S13 if not normally shut down.

In step S13, the liquid in the chambers 42, 43, 44 and 46 other than the high concentration reagent chamber 41 and the supply chamber 47 are all discarded. Specifically, the electromagnetic valves 204 and 205 are opened with the electromagnetic valves 206, 207, and 208 closed by the CPU 49a to discard the RO water in the RO water chamber 42. The RO water discarded from the RO water chamber 42 may again be transferred to the RO water producing unit 7, and new RO water may be produced from the discarded RO water. Furthermore, the electromagnetic valves 218 and 221 are opened with the electromagnetic valves 211, 212, 217, and 219 closed by the CPU 49a to push out the mixed solution in the stirring chamber 46 to the discard flow path by the positive pressure force. The electromagnetic vales 211 and 217 are then opened with the electromagnetic valves 212, 218, 219, and 221 closed by the CPU 49a to transfer the mixed solution in the diluting chamber 43 to the stirring chamber 46 with the negative pressure force, and thereafter, the mixed solution is discarded from the stirring chamber 46 by the above-described operation. The mixed solution in the diluting chamber 44 also can be transferred to the stirring chamber 46 with the negative pressure force by opening the electromagnetic valves 212 and 217 with the electromagnetic valves 211, 218, 219, and 221 closed by the CPU 49a.

Therefore, the RO water having a possibility of being accumulated for a long time is prevented from being used in the reagent preparation, and the reagent of unknown diluting magnification is prevented from being generated by discarding all liquids in the chambers 42, 43, 44, and 46 other than the high concentration reagent chamber 41 and the supply chamber 47 in step S13.

Thereafter, in step S14, the flow path, the RO water chamber 42, the diluting chamber 43 (44) and the stirring chamber 46 are cleaned. Specifically, about 12 mL (about 6 mL to each diaphragm pump) of RO water flows into the diaphragm pump 45a (45b) with the negative pressure force by opening the electromagnetic valves 206, 208, and 213 (215) by the CPU 49a after the RO water newly produced in the RO water producing unit 7 is supplied to the RO water chamber 42. The electromagnetic valves 214 (216) and 209 are then opened with the electromagnetic valve 213 (215) closed, so that about 12 mL (about 6 mL to each diaphragm pump) RO water in the diaphragm pump 45a (45b) is transferred to the diluting chamber 43 with the positive pressure force. The above operations are repeated 25 times to supply about 300 mL of newly produced RO water to the diluting chamber 43.

About 300 mL of RO water is then transferred from the diluting chamber 43 to the stirring chamber 46 by opening the electromagnetic valves 211 and 217 by the CPU 49a. The RO water in the stirring chamber 46 is discarded by opening the electromagnetic valves 218 and 221 with the electromagnetic valves 217 and 219 closed by the CPU 49a.

While the RO water is being transferred from the diluting chamber 43 to the stirring chamber 46, about 300 mL of newly produced RO water is supplied to the diluting chamber 44 through the operation similar to the operation of transferring to the diluting chamber 43. The transfer of the RO water from the diluting chamber 44 to the stirring chamber 46 is also performed through the operation similar to the operation of transferring from the diluting chamber 43 to the stirring chamber 46. Therefore, the interior of the flow path, the RO water chamber 42, the diluting chamber 43 (44), and the stirring chamber 46 are cleaned with the newly produced RO water through the series of operations described above. It is to be recognized that a predetermined amount of RO water is already stored in the RO water chamber 42 before step S13.

In step S15, the reagent is prepared in the stirring chamber 46 through the operation similar to the operation of preparing the reagent of desired concentration, and all prepared reagent are discarded. Specifically, after the reagent of the desired concentration is supplied to the stirring chamber 46 by the operations of steps S20 and S21, described later, the reagent in the stirring chamber 46 is discarded by opening the electromagnetic valves 218 and 221 with the electromagnetic valves 217 and 219 closed by the CPU 49a. Thus, even if the reagent having a concentration exceeding the desired concentration remains in the flow path, the diluting chamber 43 (44) and the stirring chamber 46, the reagent can be suppressed from being prepared to the concentration other than the desired concentration since cleaning is carried out with the reagent of the desired concentration in addition to the cleaning by the RO water.

In step S16, the RO water is supplied to the RO water chamber 42. In step S17, whether or not a predetermined amount of high concentration reagent is accommodated in the high concentration reagent chamber 41 based on the detection result of the float switch 100 by the CPU 49a. If a predetermined amount of high concentration reagent is not stored, the high concentration reagent is replenished from the high concentration reagent tank 5 to the high concentration reagent chamber 41 in step S18. Specifically, the electromagnetic valves 200 and 201 are opened with the electromagnetic valves 202 and 203 closed by the CPU 49a, so that the high concentration reagent is supplied to the high concentration reagent chamber 41 with the negative pressure force.

If a predetermined amount of high concentration reagent is accommodated in the high concentration reagent chamber 41, whether or not a predetermined amount of reagent is stored in the supply chamber 47 is determined by the CPU 49a in step S19. In other words, whether or not the reagent of greater than or equal to about 300 mL and less than or equal to about 600 mL is stored in the supply chamber 47 is determined. The process proceeds to step S26 if the predetermined amount of reagent is stored. If the predetermined amount of reagent is not stored, the electromagnetic valves 218 and 219 are opened, and the reagent is transferred from the stirring chamber 46 to the supply chamber 47. In this case, the electrical conductivity C is measured by the conductivity sensor 402, and the temperature T2 of the regent is measured by the temperature sensor 403.

In step S22, whether or not the electrical conductivity C is within a predetermined range is determined by the CPU 49a. Specifically, whether or not the measured electrical conductivity C is within the predetermined range is determined with respect to the target value Z of the electrical conductivity at the diluting magnification of 25 times calculated by equation (2). If the electrical conductivity C is not within the predetermined range, the electromagnetic valve 219 is closed and the electromagnetic valve 221 is opened, and the reagent in which the electrical conductivity C is not within the predetermined range is discarded through the discard flow path in step S23. Only the reagent diluted at satisfactory accuracy thus can be stored in the supply chamber 47.

In step S24, the electromagnetic valves 211 (212) and 217 are opened by the CPU 49a to transfer the reagent in the diluting chamber 43 (44) to the stirring chamber 46 by the negative pressure force. In this case, the transferred reagent is flowed along the inner wall of the stirring chamber 46 by the pipe 461 arranged in the stirring chamber 46 so as to be stirred in the stirring chamber 46. Thereafter, the supply processing operation of the high concentration reagent and the RO water is executed in step S25.

The supply processing operation of the high concentration reagent and the RO water in step S25 of the reagent preparation processing operation shown in FIG. 13 will be described with reference to FIGS. 6 and 14.

First, in the initial state (state immediately before reagent preparation process) of the reagent preparing device 4, the flow paths 301 to 304 shown in FIG. 6 are substantially filled with RO water and the flow path 300 is substantially filled with high concentration reagent.

Figure 14:
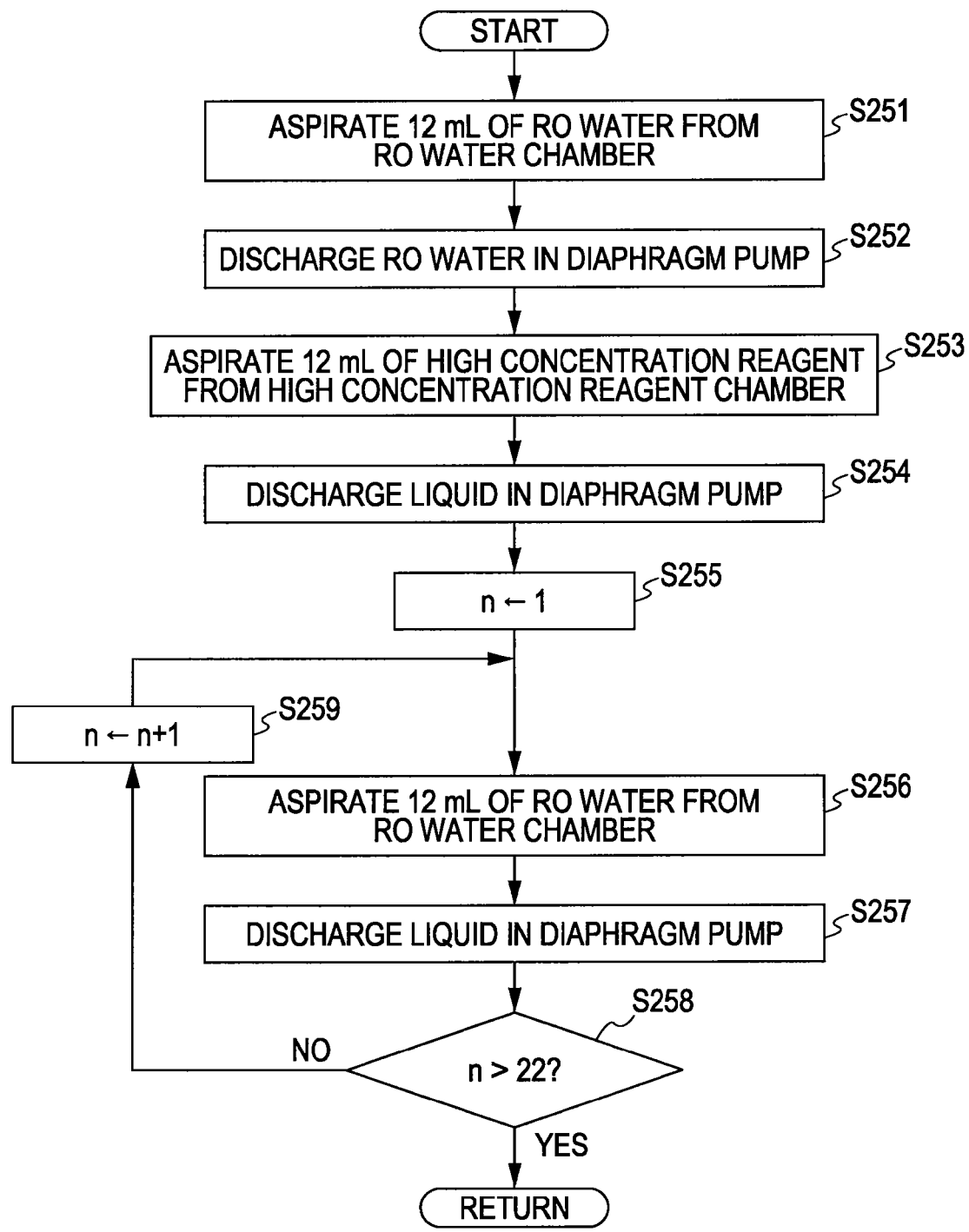
FIG. 14 is a flowchart describing the supply processing operation of the high concentration reagent and the RO water in step S25 of the reagent preparation processing operation shown in FIG. 12.

In step S251 of FIG. 14, about 12 mL (about 6 mL in each diaphragm pump) of RO water is aspirated from the RO water chamber 42 by the diaphragm pumps 45a and 45b. Specifically, the electromagnetic valves 213 (215) and 208 are opened by the CPU 49a, so that the RO water flows into the diaphragm pump 45a (45b). In step S252, the electromagnetic valves 214 (216) and 209 are opened after the electromagnetic valves 213 (215) and 208 are closed, so that positive pressure is supplied to the diaphragm pump 45a (45b) and the RO water is discharged. Thus, about 12 mL (about 6 mL in each diaphragm pump) of RO water is supplied to the diluting chamber 43 through the flow paths 301 and 303.

Thereafter, in step S253, about 12 mL (about 6 mL in each diaphragm pump) of high concentration reagent is aspirated from the high concentration reagent chamber 41 by the diaphragm pumps 45a and 45b. Specifically, the electromagnetic valves 202, 203, and 213 (215) are opened by the CPU 49a after the electromagnetic valves 214 (216) and 209 are closed, so that the negative pressure is supplied to the diaphragm pump 45a (45b) and the high concentration reagent is aspirated. Specifically, about 12 mL of high concentration reagent flowed out from the high concentration reagent chamber 41 mixes with the RO water remaining in the flow path 301, and the mixed solution of the RO water and the high concentration reagent is aspirated by the diaphragm pump 45a (45b). The mixed solution of the RO water and the high concentration reagent is filled in the flow path 301 in this case. In other words, about 12 mL of high concentration reagent flowed out from the high concentration reagent chamber 41 exists in a region combining the diaphragm pump 45a (45b) and the flow path 301 in this state. The high concentration reagent also exists in the flow path 300a, but can be substantially ignored as the amount of high concentration reagent existing in the flow path 300a is very small. Furthermore, at the time of aspirating the high concentration reagent after the second reagent preparation processing operation, the high concentration reagents remaining in the flow path 300a from the previous reagent preparation processing operation is pushed out to the flow path 301 side, and thus about 12 mL of high concentration reagent more accurately exists in the region combining the diaphragm pump 45a (45b) and the flow path 301.

In step S254, the electromagnetic valves 214 (216) and 209 are opened after the electromagnetic valves 202, 203, and 213 (215) are closed, so that positive pressure is supplied and the mixed solution of RO water and high concentration reagent is discharged from the diaphragm pump 45a (45b). Thus, the mixed solution of RO water and high concentration reagent is supplied to the diluting chamber 43 through the flow paths 301 and 303. In this case, a few mL of high concentration reagent remains mixed with the RO water in the flow paths 301 and 303.

In step S255, n=1 is set by the CPU 49a. Here, n is the number of discharging of the RO water by the diaphragm pumps 45a and 45b, and is defined with a real number starting from 1. In step S256, about 12 mL of RO water is aspirated from the RO water chamber 42 by the diaphragm pumps 45a and 45b, similar to step S251. Similar to step S252, in step S257, the RO water is discharged from the diaphragm pumps 45a and 45b. Thus, the high concentration reagent remaining in the flow paths 301 and 303 is transferred to the diluting chamber 43 with the RO water.

Thereafter, in step S258, whether or not n is greater than 22 is determined by the CPU 49a. If n is not greater than 22, n=n+1 is set in step S259, and the operations of steps S256 to S259 are repeated until n becomes greater than 22. In other words, the operations of steps S256 to S259 are repeated until the aspiration and discharge operation of the RO water are performed 24 times with respect to one aspiration and discharge operation of the high concentration reagent by the diaphragm pumps 45a and 45b. The operation is terminated when n is greater than 22. Thus, about 12 mL×24 times=about 288 mL of RO water and about 12 mL×1 time=about 12 mL of high concentration reagent, or the mixed solution of about 288 mL+about 12 mL=about 300 mL is supplied to the diluting chamber 43. After the aspiration and discharge operation of the high concentration reagent by the diaphragm pumps 45a and 45b, the aspiration and discharge operation of the RO Water is performed 23 times, and thus the high concentration reagent remaining in the flow paths 301 and 303 are all transferred to the diluting chamber 43, and only the RO water consequently exists in the flow paths 301 and 303.

In the above operation, if the electromagnetic valve 210 is driven in place of the electromagnetic valve 209, about 300 mL of mixed solution containing about 288 mL of RO water and about 12 mL of high concentration reagent can be transferred to the diluting chamber 44.

Figure 13:
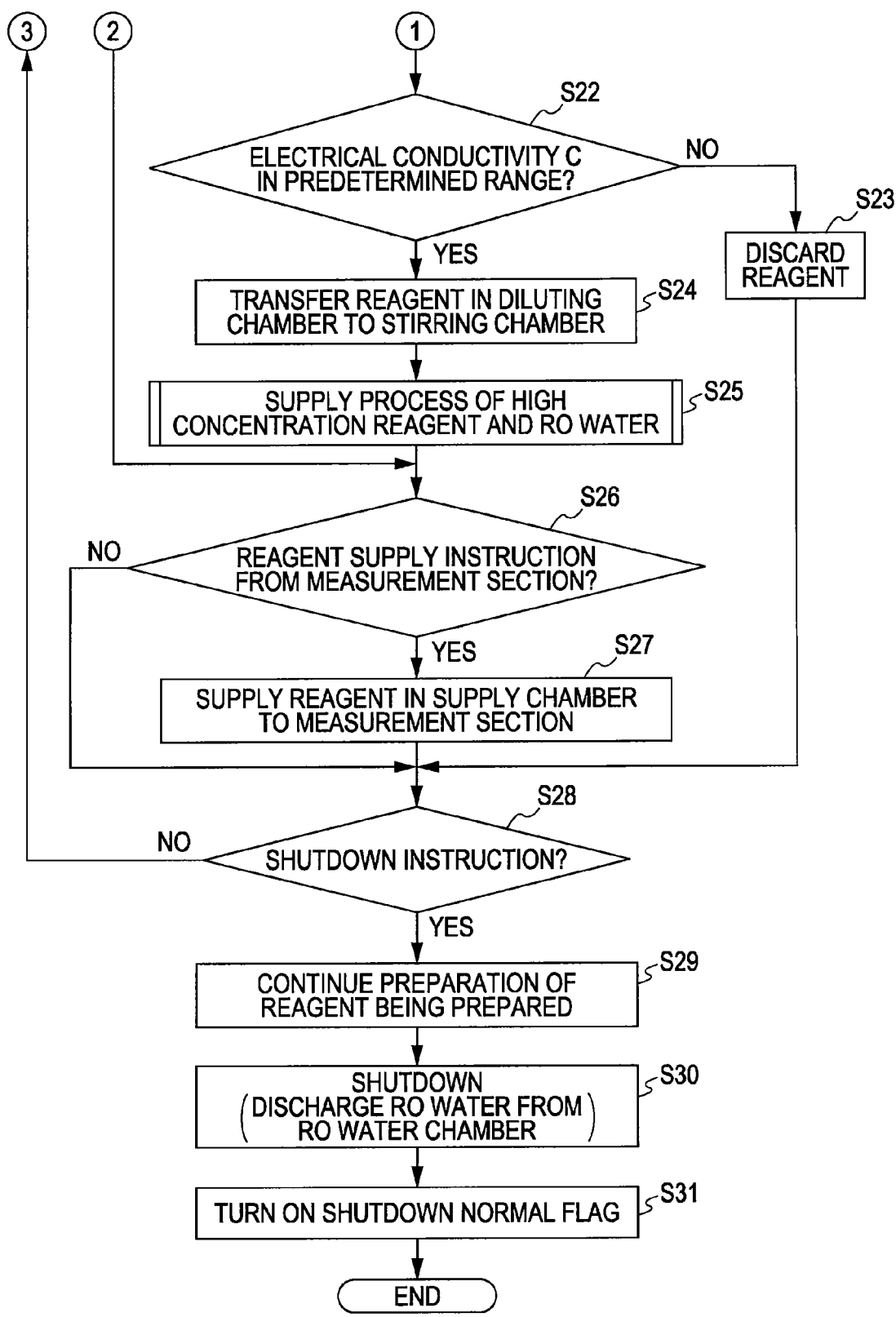
FIG. 13 is a flowchart explaining the reagent preparation processing operation of the reagent preparing device according to the first embodiment of the present invention.

After the supply process of the high concentration reagent and the RO water is performed in step S25 of FIG. 13, whether a reagent supply instruction from the measurement section 2 transmitted through the data processing section 3 is made is determined by the CPU 49a in step S26, where the process proceeds to step S28 if the instruction is not made. If the reagent supply instruction is made, the reagent in the supply chamber 47 is transferred to the measurement section 2 through the filter 471 by the negative pressure force supplied from the measurement section 2 in step S27. The presence of shutdown instruction from the user is then determined by the CPU 49a in step S28, where the process proceeds to step S16 if the instruction is not made. The reagent to be transferred to the supply chamber 47 is discontinuously prepared, and the reagents prepared at different times are simultaneously stored in the supply chamber 47 by the operations of steps S19 to S25.

If the shutdown instruction is made, the above operation is continued until the reagent in the middle of the preparation is ultimately transferred to the supply chamber 47 in step S29. Specifically, since the reagent preparation is continued by the operation of steps S19 to S25, the reagent diluted to a concentration different from the desired concentration remains in the flow path, the diluting chamber 43 (44) and the stirring chamber 46 if the operation is stopped in the middle of preparation. Thus, the reagent diluted to a concentration different from the desired concentration is prevented from remaining in the flow path, the diluting chamber 43 (44), and the stirring chamber 46 by continuing the preparation operation in step S29.

Figure 15:
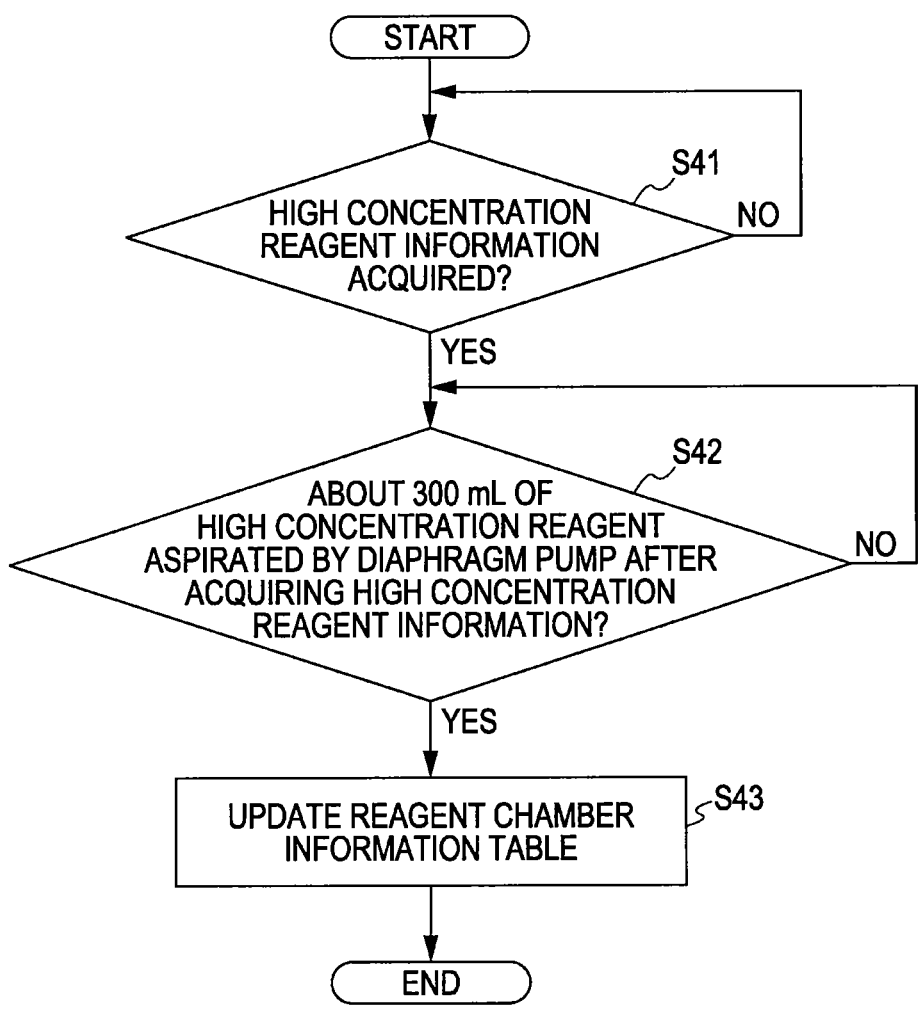
FIG. 15 is a flowchart describing an update processing operation of a reagent chamber information table of the reagent preparing device according to the first embodiment of the present invention.
Figure 16:
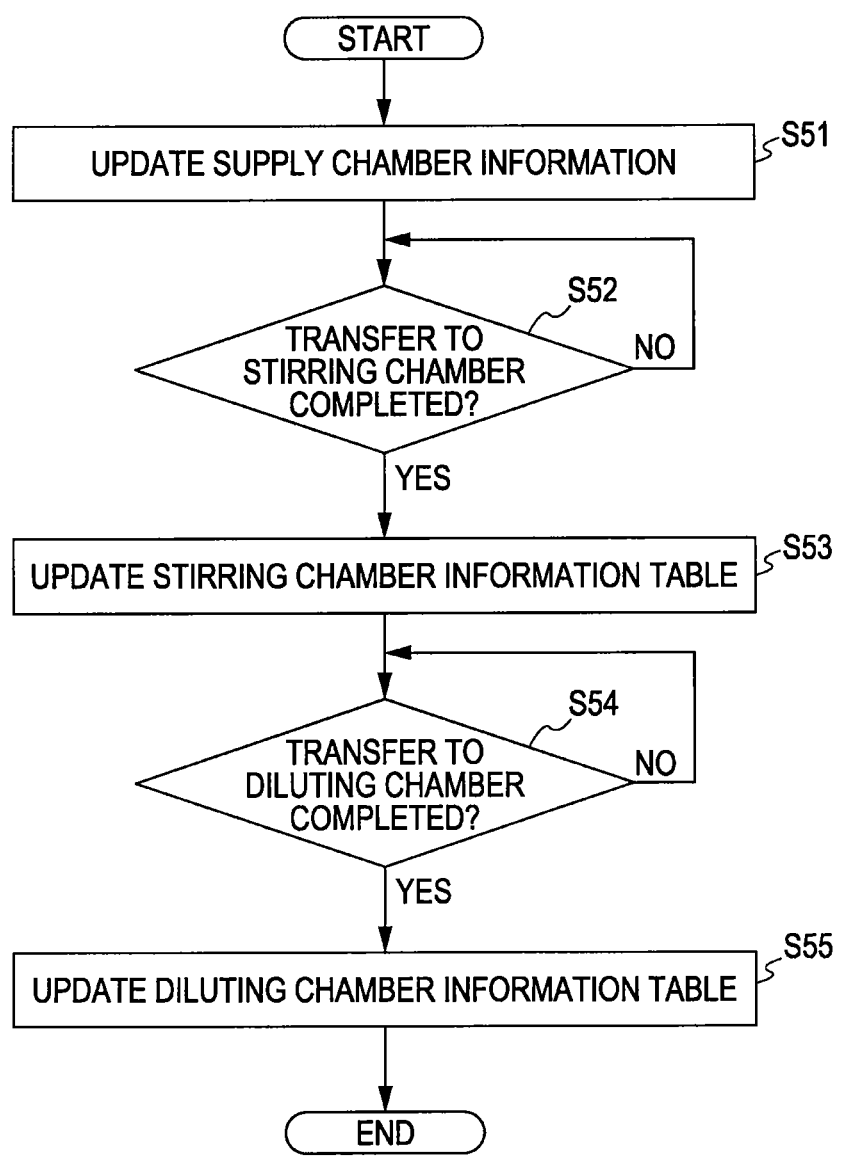
FIG. 16 is a flowchart describing an update processing operation of a diluting chamber information table A (B), a stirring chamber information table, and a supply chamber information table of the reagent preparing device according to the first embodiment of the present invention.

In step S30, the shutdown is executed. In this case, the RO water is discharged from the RO water chamber 42. The RO water is thus prevented from being accumulated in the RO water chamber 42 until the reagent preparing device 4 is activated at the next time. Thereafter, in step S31, the flag indicating that the shutdown is normally performed is set to ON, and the reagent preparation processing operation is terminated. The reagent preparation process shown in FIGS. 12 and 13, the updating process of the reagent chamber information table 492, to be hereinafter described, shown in FIG. 15, and the updating process of the diluting chamber information table A493, the diluting chamber information table B494, the stirring chamber information table 495, and the supply chamber information table 496, to be hereinafter described, shown in FIG. 16 are continuously executed in parallel while the reagent preparing device 4 is operating by the CPU 49a.

The update processing operation of the reagent chamber information table of the reagent preparing device 4 according to the first embodiment of the present invention will now be described with reference to FIG. 15.

First, in step S41, whether or not the high concentration reagent information is acquired is determined by the CPU 49a. Specifically, the CPU 49a determines whether or not the pre-opening expiration date, the post-opening expiration date information, and the like are acquired by the high concentration reagent information acquisition processing operation of the reagent preparing device 4 shown in FIG. 9. The CPU 49a repeats the determination until the high concentration reagent information is acquired, and when the high concentration reagent information is acquired, the CPU 49a determines whether or not about 300 mL of high concentration reagent, or accommodation upper limit amount of the high concentration reagent chamber 41, is aspirated by the diaphragm pump 45a (45b) after acquiring the high concentration reagent information in step S42. Specifically, about 12 mL (about 6 mL with each pump) of high concentration reagent is aspirated by one aspirating operation of the diaphragm pump 45a (45b). Therefore, if the aspirating operation is performed 25 times to aspirate the high concentration reagent by the diaphragm pump 45a (45b), about 300 mL (about 12 mL×25 times=about 300 mL) of high concentration reagent is aspirated from the high concentration reagent chamber 41. Thus, after the high concentration reagent information is acquired by the CPU 49a, whether or not the aspirating operation is performed 25 times by the diaphragm pump 45a (45b) to aspirate the high concentration reagent from the high concentration reagent chamber 41 is determined to determine whether or not about 300 mL of high concentration reagent is aspirated from the high concentration reagent chamber 41 after acquiring the high concentration reagent information.

The CPU 49a repeats the determination until about 300 mL of high concentration reagent is aspirated from the high concentration reagent chamber 41 after acquiring the high concentration reagent information, and the process proceeds to step S43 when about 300 mL of high concentration reagent is aspirated. In step S43, the CPU 49a updates the reagent chamber information table 492. Specifically, the CPU 49a updates the reagent chamber information table 492 of the storage portion 49f based on the pre-opening expiration date information and the post-opening expiration date information acquired by the high concentration reagent information acquisition processing operation shown in FIG. 9 and recorded in the reagent management list 491 of the storage portion 49f. More specifically, the CPU 49a rewrites the pre-opening expiration date information and the post-opening expiration date information of the reagent chamber information table 492 to the information of the same content as the most recent (immediate) pre-opening expiration date information and the post-opening expiration date information recorded in the reagent management list 491.

Therefore, after the high concentration reagent information is acquired, that is, after the high concentration reagent tank 5 is replaced, about 300 mL of high concentration reagent is aspirated from the high concentration reagent chamber 41, and the reagent chamber information table 492 is thereafter updated so that the reagent chamber information table 492 is updated after substantially all old high concentration reagent of before the replacement is aspirated from the high concentration reagent chamber 41, and thus a more stricter management in terms of expiration date can be performed compared to when updating the reagent chamber information table 492 immediately after replacing the high concentration reagent tank 5.

The update processing operation of the diluting chamber information table A(B), the stirring chamber information table, and the supply chamber information table of the reagent preparing device 4 according to the first embodiment of the present invention will now be described with reference to FIG. 16.

The update processing operation starts when the reagent in the stirring chamber 46 passes the conductivity sensor 402 and the electrical conductivity C of the reagent is within a predetermined range. In step S51, the CPU 49*a* updates the supply chamber information table 496 of the storage portion 49*f*. Specifically, the CPU 49*a* records the information on the reagent passed through the conductivity sensor 402 and supplied to the supply chamber 47 this time in the supply chamber information table 496 in place of the oldest information of the information on the most recent three reagents (three reagents transferred to the supply chamber 47 immediately before) recorded in the supply chamber information table 496. In this case, the newly recorded pre-opening expiration date information and the post-opening expiration date information respectively have the same content as the pre-opening expiration date information and the post-opening expiration date information of the stirring chamber information table 495 at the current time point. The flow-in time information newly recorded in this case is the time at which the reagent to be transferred to the supply chamber 47 this time passed through the conductivity sensor 402.

Subsequently, in step S52, whether or not the transfer of a mixed solution to the stirring chamber 46 is completed is determined by the CPU 49*a*. Specifically, when the reagent is transferred from the stirring chamber 46 to the supply chamber 47, and the float portion of the float switch 105 in the stirring chamber 46 reaches the lower limit and the chamber becomes empty, about 300 mL of mixed solution is supplied from either diluting chamber 43 or 44 to the stirring chamber 46. The CPU 49*a* determines whether or not about 300 mL of mixed solution is transferred from either diluting chamber 43 or 44 to the stirring chamber 46.

This determination is repeated until the transfer of about 300 mL of mixed solution to the stirring chamber 46 is completed, and when the transfer is completed, the CPU 49*a* updates the stirring chamber information table 495 in step S53. Specifically, the CPU 49*a* updates the pre-opening expiration date information and the post-opening expiration date information of the stirring chamber information table 495 to the information of the same content as the pre-opening expiration date information and the post-opening expiration date information of the diluting chamber information table A493 (diluting chamber information table B494) at the current time point corresponding to the diluting chamber 43 (44) or the supply source of the mixed solution.

Thereafter, in step S54, whether or not the transfer of the mixed solution to the diluting chamber 43 (44) that supplied the mixed solution to the stirring chamber 46 is completed is determined by the CPU 49*a*. Specifically, when the mixed solution is transferred from the diluting chamber 43 (44) to the stirring chamber 46, and the float portion of the float switch 103 (104) in the diluting chamber 43 (44) reaches the lower limit and the chamber becomes empty, about 300 mL of mixed solution (about 12 mL of high concentration reagent and about 288 mL of RO water) is supplied to the empty diluting chamber 43 (44) by the diaphragm pump 45*a* (45*b*). The CPU 49*a* determines whether or not about 300 mL of mixed solution is transferred to the diluting chamber 43 (44) by the supply processing operation of the high concentration reagent and the RO water shown in FIG. 14.

This determination is repeated until the transfer of about 300 mL of mixed solution to the empty diluting chamber 43 (44) is completed, and when the transfer is completed, the CPU 49*a* updates the diluting chamber information table A493 (diluting chamber information table B494) corresponding to the diluting chamber 43 (44) in which transfer of the mixed solution is completed in step S55. Specifically, the CPU 49*a* updates the pre-opening expiration date information and the post-opening expiration date information of the diluting chamber information table A493 (diluting chamber information table B494) to the information of the same content as the pre-opening expiration date information and the post-opening expiration date information of the reagent chamber information table 492 at the current time point.

Figure 17:
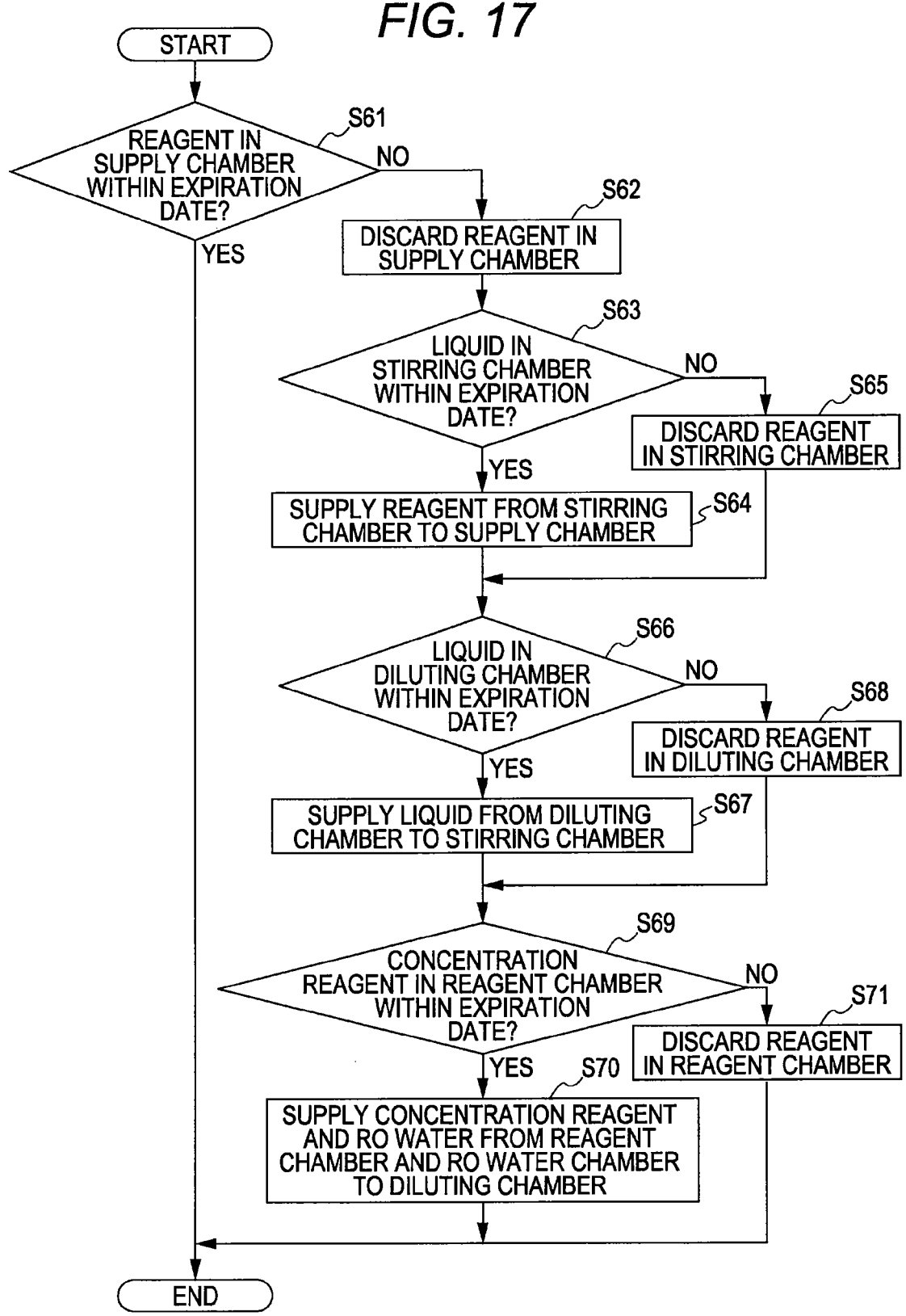
FIG. 17 is a flowchart describing an expiration date monitor processing operation of the reagent preparing device according to the first embodiment of the present invention.

An expiration date monitor processing operation of the reagent preparing device 4 according to the first embodiment of the present invention will now be described with reference to FIG. 17.

The expiration date monitor processing operation is executed when the reagent preparing device 4 first performs the preparing operation after change of date. First, in step S61, the CPU 49*a* determines whether or not the reagent in the supply chamber 47 is within the expiration date based on the supply chamber information table 496. Specifically, the CPU 49*a* selects the oldest expiration date of the pre-opening expiration date information and the post-opening expiration date information of the information on three reagents recorded in the supply chamber information table 496, and determines whether the selected oldest expiration date is older than the current date. In other words, the CPU 49*a* determines whether the expiration date of the reagent having the oldest expiration date is no longer valid of the reagents having a possibility of being stored in the supply chamber 47. Whether or not supply of reagent to the measurement section 2 is possible is then determined. If the expiration date of the reagent in the supply chamber 47 is still valid, the expiration date monitor processing operation is terminated as is.

If the expiration date of the reagent with the oldest expiration date in the supply chamber 47 is not valid, the CPU 49*a* discards the reagent in the supply chamber 47 in step S62. Specifically, the electromagnetic valve 220 is opened and the reagent in the supply chamber 47 is discharged to the discard flow path by the CPU 49*a*.

Thereafter, in step S63, the CPU 49*a* determines whether or not the reagent in the stirring chamber 46 is within the expiration date based on the stirring chamber information table 495. Specifically, the CPU 49*a* determines whether or not the pre-opening expiration date information and the post-opening expiration date information of the stirring chamber information table 495 are both within the expiration date. If the pre-opening expiration date information and the post-opening expiration date information are both within the expiration date, the CPU 49*a* transfers the reagent in the stirring chamber 46 to the supply chamber 47 in step S64. Specifically, the CPU 49*a* opens the electromagnetic valves 218 and 219, and pushes out the reagent in the stirring chamber 46 with the positive pressure force. In this case, the reagent in the supply chamber 47 is already discarded in step S62 even if the reagent in the supply chamber 47 cannot be supplied to the measurement section 2, and thus the mixed solution transferred from the stirring chamber 46 to the supply chamber 47 is prevented from mixing with the reagent in the supply chamber 47 to be discarded. If either the pre-opening expiration date information or the post-opening expiration date information is expired, the CPU 49*a* opens the electromagnetic valves 218 and 221 to discharge the reagent in the stirring chamber 46 to the discard flow path in step S65.

In step S66, the CPU 49a determines whether or not the reagents in the diluting chambers 43 and 44 are respectively within the expiration date based on the diluting chamber information table 493A and the diluting chamber information table 493B. Specifically, the CPU 49a determines whether or not the pre-opening expiration date information and the post-opening expiration date information of the diluting chamber information table 493A (diluting chamber information table 493B) are both within the expiration date. If the pre-opening expiration date information and the post-opening expiration date information on the reagent in the diluting chamber 43 (44) are both within the expiration date, the CPU 49a transfers the mixed solution in the diluting chamber 43 (44) to the stirring chamber 46 in step S67. Specifically, the CPU 49a opens the electromagnetic valves 211 (212) and 217, and aspirates the reagent in the diluting chamber 43 (44) with the negative pressure force. If either the pre-opening expiration date information or the post-opening expiration date information is expired, the CPU 49a transfers the mixed solution from the diluting chamber 43 (44) to the stirring chamber 46 and discharges the mixed solution from the stirring chamber 46 to the discard flow path through the electromagnetic valve 221 in step S68. The CPU 49a makes the determination separately for the reagents in the diluting chambers 43 and 44, respectively.

In step S69, the CPU 49a determines whether or not the high concentration reagent in the high concentration reagent chamber 41 is within the expiration date based on the reagent chamber information table 492. Specifically, the CPU 49a determines whether within the expiration date for both the pre-opening expiration date information and the post-opening expiration date information of the reagent chamber information table 492. Whether or not the high concentration reagent in the high concentration reagent chamber 41 can be used to prepare the reagent is then determined. If both the pre-opening expiration date information and the post-opening expiration date information of the high concentration reagent in the high concentration reagent chamber 41 are within the expiration date, the CPU 49a drives the diaphragm pump 45a (45b) and transfers the high concentration reagent in the high concentration reagent chamber 41 and the RO water in the RO water chamber 42 to the diluting chamber 43 (44) in step S70. If either the pre-opening expiration date information or the post-opening expiration date information is expired, the CPU 49a opens the electromagnetic valves 202 and 222, and discharges the high concentration reagent from the high concentration reagent chamber 41 to the discard flow path in step S71.

The RO water automatic discharge processing operation according to the first embodiment of the present invention will now be described with reference to FIGS. 6 and 18. The processes of steps S81 to S87 shown in FIG. 18 are continuously executed in parallel with the reagent preparation processing operation shown in FIGS. 12 and 13 from when the reagent preparing device 4 is activated until shut down.

Figure 18:
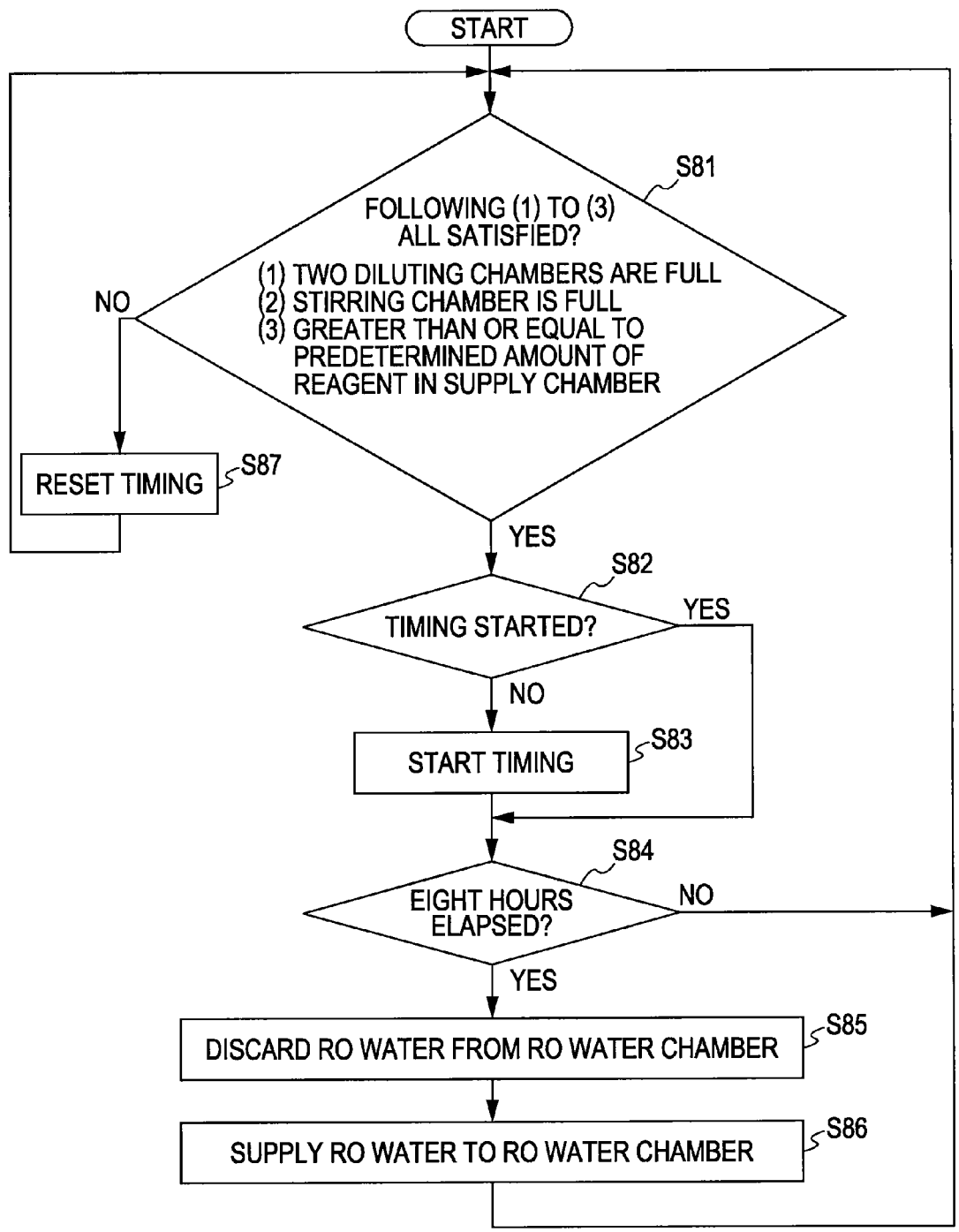
FIG. 18 is a flowchart explaining an RO water automatic discharge processing operation of the reagent preparing device according to the first embodiment of the present invention.

First, in step S81 of FIG. 18, whether or not a predetermined condition is satisfied is determined by the CPU 49a. Specifically, whether or not the following three conditions are all satisfied is determined. The first condition is that the two diluting chambers 43 and 44 shown in FIG. 6 are both filled with about 300 mL of mixed solution; the second condition is that the stirring chamber 46 is filled with about 300 mL of mixed solution, and the third condition is that the supply chamber 47 is stored with greater than or equal to about 300 mL and less than or equal to about 600 mL of reagent of the desired concentration. If all three conditions are satisfied, a new reagent preparation process is not required, and thus the RO water is accumulated in the RO water chamber 42 without the RO water in the RO water chamber 42 being used. In other words, determination is made that the RO water in the RO water chamber 42 is no longer used by determining whether all three conditions are satisfied by the CPU 49a.

If all three conditions are satisfied (i.e., if RO water in the RO water chamber 42 is no longer used), whether or not timing started is determined by the CPU 49a in step S82, and the process proceeds to step S84 if timing is already started. If timing is not started, the timing is started in step S83. Thereafter, whether or not eight hours have elapsed from the start of timing is determined in step S84, and the process returns to step S81 if eight hours have not elapsed.

If eight hours have elapsed from the start of timing, the RO water in the RO water chamber 42 is discarded in step S85. Specifically, the RO water in the chamber is pushed out to the discard flow path with the positive pressure force by opening the electromagnetic valves 204 and 205 with the electromagnetic valves 206, 207, and 208 closed by the CPU 49a. The RO water accumulated in the RO water chamber 42 for a long time (eight hours) can thus be discarded. The RO water discarded from the RO water chamber 42 may again be transferred to the RO water producing unit 7, and new RO water may be produced from the discarded RO water. After all RO water in the RO water chamber 42 is discarded, the electromagnetic valves 204, 205, and 208 are closed and the electromagnetic valves 206 and 207 are opened by the CPU 49a in step S86, so that the RO water newly produced in the RO water producing unit 7 is supplied to the RO water chamber 42.

If at least one condition of the three conditions is not satisfied in step S81, the timing is reset in step S87, and the process returns to step S81. Since the RO water in the RO water chamber 42 is discarded when accumulated for a long time (eight hours) by the RO water automatic discharge processing operation, the expiration date does not need to be monitored.

In the first embodiment, determination can be made that the prepared reagent that is not suited for analysis in terms of expiration date cannot be supplied to the measurement section 2 by configuring the CPU 49a so as to determine whether or not the prepared reagent stored in the supply chamber 47 can be supplied to the measurement section 2 based on the pre-opening expiration date information and the post-opening expiration date information of the high concentration reagent recorded in the supply chamber information table 496, and thus the prepared reagent that is not suited for analysis in terms of expiration date can be prevented from being supplied to the measurement section 2.

In the first embodiment, the conductivity sensor 402 for detecting the flow to reagent to the supply chamber 47 is arranged, and the CPU 49a is configured to update the supply chamber information table 496 stored in the storage portion 49f when the flow of reagent to the supply chamber 47 is detected by the conductivity sensor 402, and thus the supply chamber information table 496 is updated every time the reagent flows into the supply chamber 47, and whether or not the prepared reagent stored in the supply chamber 47 can be supplied to the measurement section 2 can be determined based on the most recent expiration date information.

Furthermore, in the first embodiment, the reagents prepared at different times are simultaneously stored in the supply chamber 47 and the expiration date information for three reagents are recorded in the supply chamber information table 496 of the storage portion 49f, and the CPU 49a is configured to select the oldest expiration date of the pre-opening expiration date information and the post-opening expiration date information of the expiration date information for three reagents and determine whether or not the prepared reagent stored in the supply chamber 47 can be supplied to the measurement section 2 based on the selected oldest expiration date, and hence whether or not the prepared reagent stored in the supply chamber 47 can be supplied to the measurement section 2 can be supplied to the measurement section 2 can be determined based on the oldest expiration date information of the reagent in the supply chamber 47 even if the reagents prepared at different times are stored in the supply chamber 47, and the prepared reagent that is not suited for analysis in terms of expiration date is accurately prevented from being supplied to the measurement section 2 even when the reagents prepared at different times are stored in the supply chamber 47.

In the first embodiment, the CPU 49a is configured to determine whether or not the mixed solution stored in the stirring chamber 46 can be supplied to the supply chamber 47 based on the stirring chamber information table 495, and control the electromagnetic valves 218 and 221 to discard the mixed solution stored in the stirring chamber 46 when determined as not suppliable, and thus the mixed solution before preparation that is not suited for analysis in terms of expiration date can be prevented from being supplied to the supply chamber 47 since the mixed solution before preparation determined as not suppliable is discarded from the stirring chamber 46.

In the first embodiment, the CPU 49a is configured to supply the mixed solution from the stirring chamber 46 to the supply chamber 47 after the prepared reagent stored in the supply chamber 47 is discarded when determined that the prepared reagent in the supply chamber 47 cannot be supplied to the measurement section 2 and determined that the mixed solution in the stirring chamber 46 can be supplied to the stirring chamber 46, and thus the mixed solution before preparation in the stirring chamber 46 that does not have any problems in terms of expiration date can be supplied to the supply chamber 47 after the prepared reagent in the supply chamber 47 that is not suited for analysis in terms of expiration date is discarded, and the prepared reagent that is not suited for analysis in terms of expiration date and the mixed solution before preparation that does not have any problems in terms of expiration date are prevented from being mixed in the supply chamber 47 and become unsuited for analysis in terms of expiration date as a whole. The mixed solution before preparation in the stirring chamber 46 that does not have any problems in terms of expiration date is thereby suppressed from becoming a waste.

In the first embodiment, the CPU 49a is configured to determine whether or not the high concentration reagent in the high concentration reagent chamber 41 can be used to prepare the reagent based on the reagent chamber information table 492, and control the electromagnetic valves 202 and 222 to discard the high concentration reagent in the high concentration reagent chamber 41 when determined that the high concentration reagent in the high concentration reagent chamber 41 cannot be used to prepare the reagent, and thus the high concentration reagent that is not suited for preparation of reagent in terms of expiration date can be discarded and the high concentration reagent that is not suited for preparation of reagent in terms of expiration date is prevented from being used to prepare the reagent.

Second Embodiment

A second embodiment will be described with reference to FIGS. 19 and 20. In the second embodiment, a reagent preparing device 500 interiorly including the RO water producing unit 7 will be described, different from the first embodiment.

Figure 19:
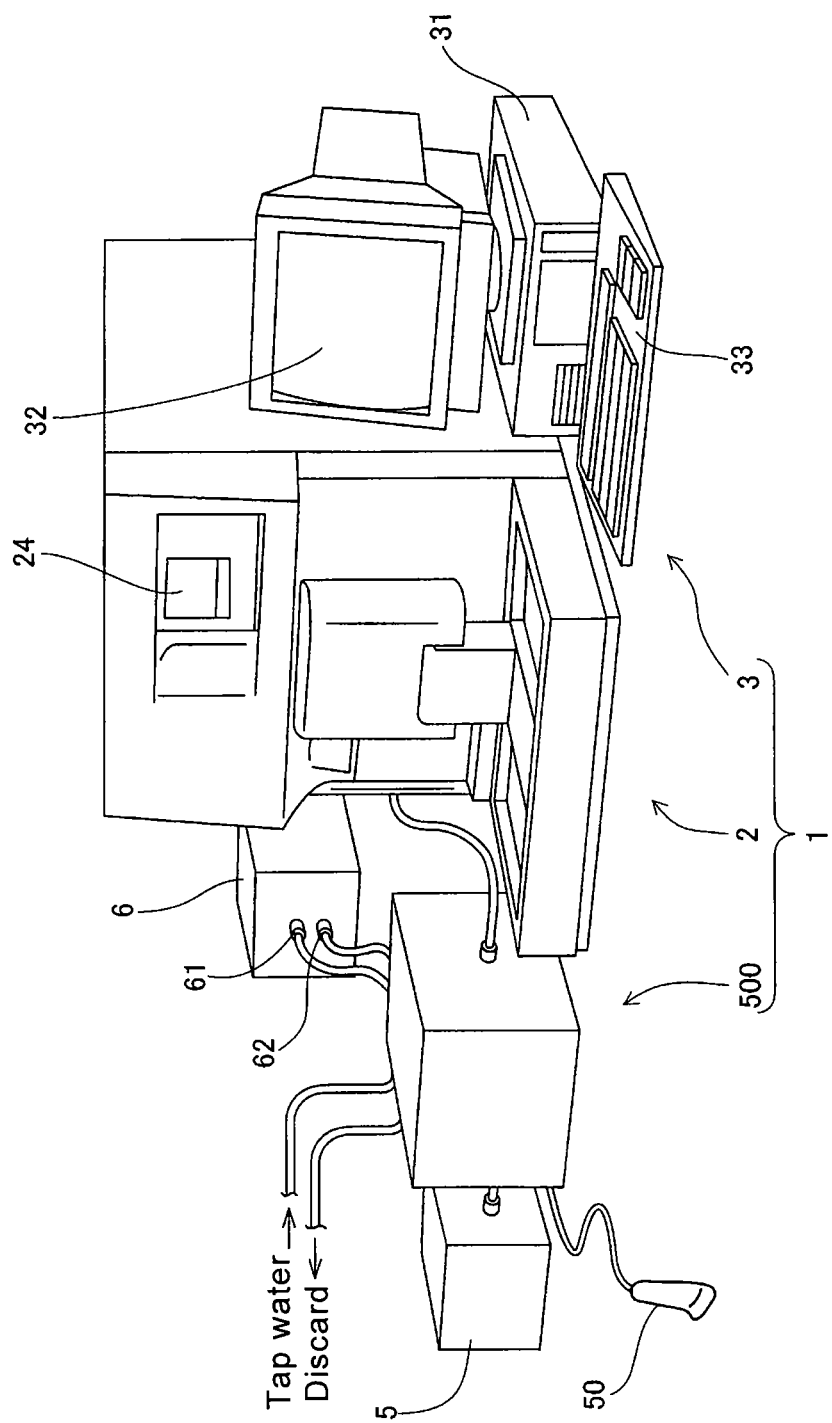
FIG. 19 is a perspective view showing a usage mode of a reagent preparing device according to a second embodiment of the present invention.

As shown in FIG. 19, the blood specimen processing system 1 is configured by the measurement section 2 having a function of measuring blood, the data processing section 3 for analyzing the measurement data output from the measurement section 2 and obtaining an analysis result, and the reagent preparing device 500 for preparing a reagent to be used in the processing of specimens.

Figure 20:
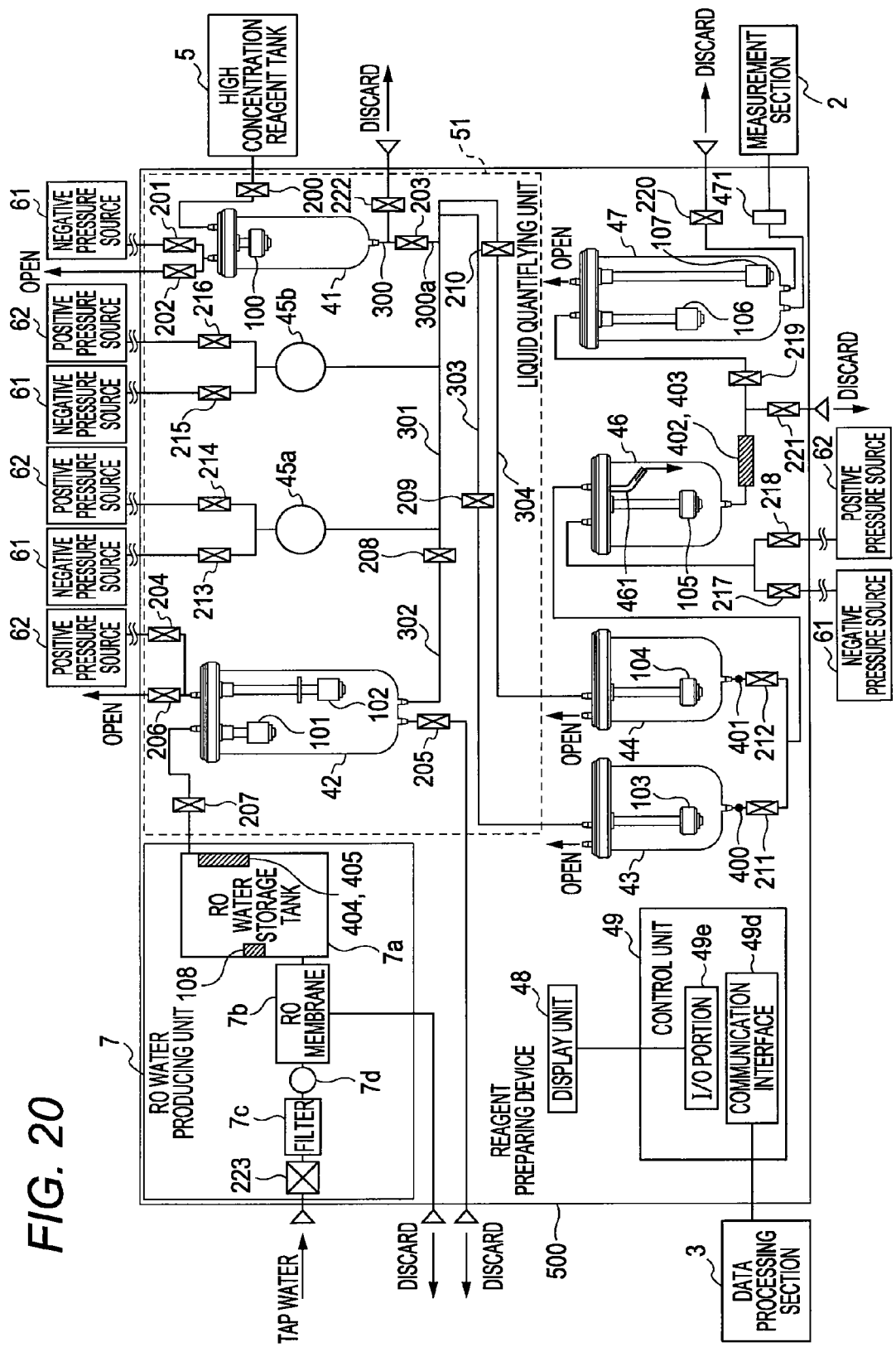
FIG. 20 is a block diagram showing a configuration of a reagent preparing device according to the second embodiment of the present invention.

As shown in FIGS. 19 and 20, in the second embodiment, the reagent preparing device 500 is configured to prepare the reagent to be used in blood analysis by diluting the high concentration reagent to a desired concentration using the RO water produced by the interiorly arranged RO water producing unit 7.

The reagent preparing device 500 does not include a display unit, as opposed to the first embodiment. Thus, the user activates and shuts down the reagent preparing device 4 using the input device 33 of the data processing section 3.

Other structures of the second embodiment are similar to those of the first embodiment.

In the second embodiment, the configuration of the entire blood specimen processing system 1 can be facilitated by arranging the RO water producing unit 7 inside the reagent preparing device 500.

Other effects of the second embodiment are similar to the first embodiment.

The embodiments disclosed herein are illustrative in all aspects and should not be construed as being exclusive. The scope of the present invention is defined by the Claims rather than by the description of the embodiments made above, and all modifications equivalent in meaning to the Claims and within the scope of the Claims are to be encompassed.

For instance, in the first embodiment and the second embodiment, an example of discarding the RO water from the RO water chamber when the RO water is accumulated for a long time (eight hours) with timing the accumulation time of the RO water has been described, but the present invention is not limited thereto, and the expiration date of the RO water in the RO water chamber may be monitored and the RO water may be discarded from the RO water chamber when expired without timing the accumulation time of the RO water.

In the first embodiment and the second embodiment, an example of a configuration of preparing the reagent from the high concentration reagent and the RO water by the reagent preparing device has been described, but the present invention is not limited thereto, and a configuration of preparing the reagent from a plurality of different types of liquids other than the high concentration reagent and the RO water by the reagent preparing device may be adopted.

In the first embodiment and the second embodiment, an example of configuring the supply chamber information table to record the pre-opening expiration date information, the post-opening expiration date information, and the flow-in time information for the three most recent reagents (three reagents transferred to the supply chamber immediately before), but the present invention is not limited thereto, and the supply chamber information table may be configured to record the pre-opening expiration date information, the post-opening expiration date information and the flow-in time information of less than three reagents or more than three reagents. In this case, whether or not the reagent can be supplied to the measurement section can be determined with conditions stricter according to the expiration date the greater the recordable number.

In the first embodiment and the second embodiment, the supply chamber information table is updated by the CPU when the reagent passes the conductivity sensor and the electrical conductivity C of the reagent is within a predetermined range, but the present invention is not limited thereto, and determination may be made that the new reagent is supplied to the supply chamber based on the detection result of the float switch in the supply chamber by the CPU, and the supply chamber information table may be updated when determined that the reagent is supplied.

In the first embodiment and the second embodiment, the CPU determines whether the aspirating operation is performed 25 times by the diaphragm pump to aspirate the high concentration reagent from the high concentration reagent chamber after replacing the high concentration reagent tank and acquiring the high concentration reagent information, and updates the reagent chamber information table when the aspirating operation is performed 25 times, but the present invention is not limited thereto, and all high concentration reagents in the high concentration reagent chamber may be discarded when the high concentration reagent information is acquired, and thereafter, the new high concentration reagent may be supplied to the high concentration reagent chamber and the reagent chamber information table may be updated.

In the first embodiment and the second embodiment, the reagent preparing device for monitoring the pre-opening expiration date and the post-opening expiration date of the high concentration reagent has been described, but the present invention is not limited thereto, and the elapsed time from the preparation of the reagent stored in the supply chamber 47 may be monitored and the reagent stored in the supply chamber 47 may be discarded regardless of the pre-opening expiration date and the post-opening expiration date of the high concentration reagent when the elapsed time exceeds a predetermined expiration date.

In the first embodiment and the second embodiment, the reagent preparing device for monitoring the pre-opening expiration date and the post-opening expiration date of the high concentration reagent, and automatically discarding the reagent stored in the supply chamber 47 when the expiration date is exceeded has been described, but the present invention is not limited thereto, and a warning may be displayed on the display unit 48 and the reagent stored in the supply chamber 47 may be manually discharged by the user when the expiration date is exceeded.

Furthermore, in the first embodiment and the second embodiment, the pre-opening expiration date is stored in the storage portion 49f based on the barcode 50b, but the input from the user of the reagent preparing device may be accepted through the display unit 32, and stored in the storage portion 49f.

Figure 21:
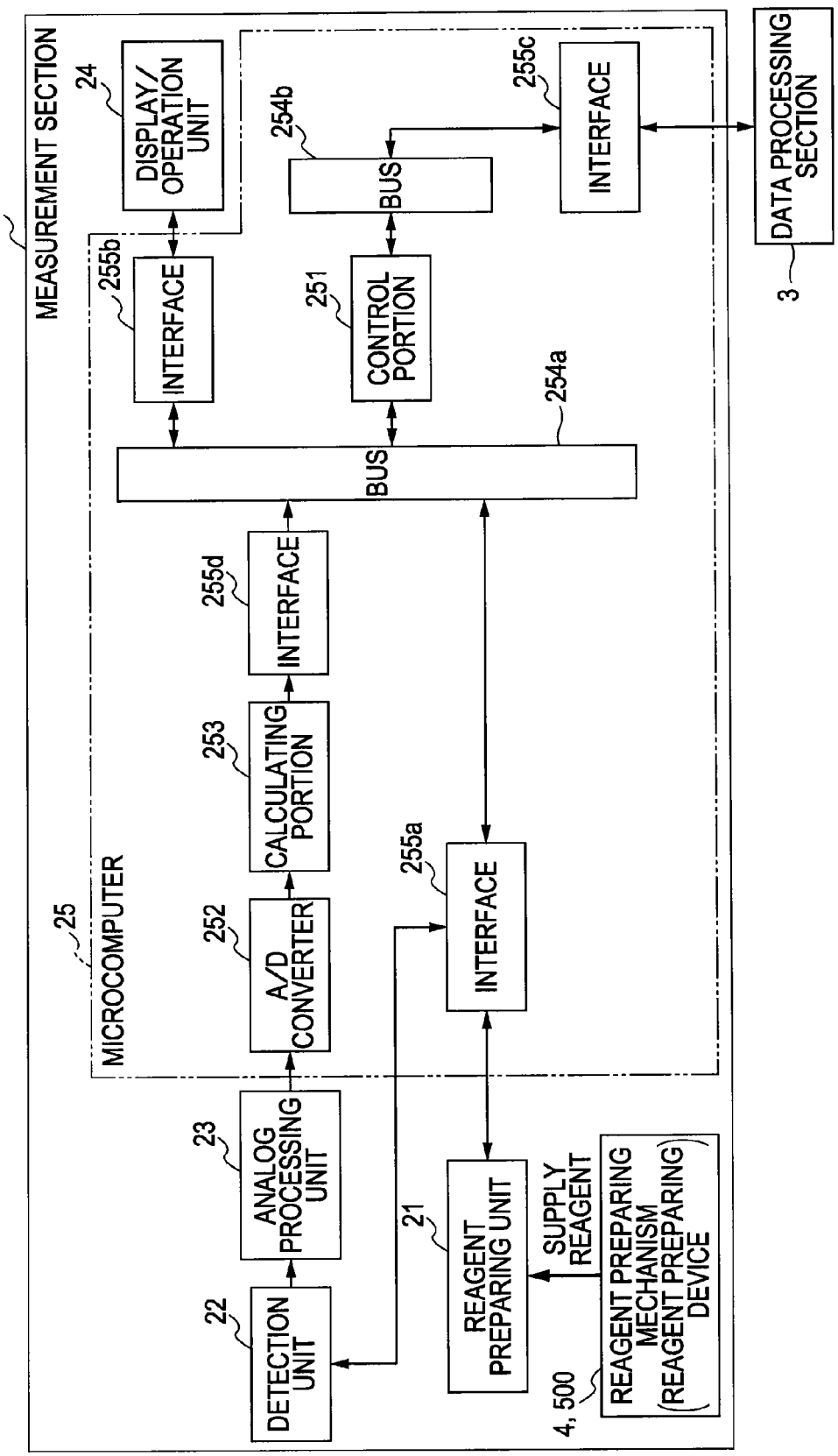
FIG. 21 is a block diagram explaining a variant of the reagent preparing device according to the first embodiment shown in FIG. 1 and the second embodiment shown in FIG. 19.

In the first embodiment and the second embodiment, the reagent preparing device installed separate from the measurement section has been described as one example of the reagent preparing device, but the present invention is not limited thereto, and it may be a reagent preparing device arranged in the measurement section and having a function of a reagent preparing mechanism, as shown in FIG. 21. The measurement section (device) equipped with the reagent preparing mechanism includes blood cell counting device, immune measurement device, and smear producing device, but is particularly suited to the blood cell counting device in which the usage amount of the diluting liquid is large.

What is claimed is:

1. A reagent preparing device connected to a measurement section that analyzes a specimen with a reagent prepared by and supplied from the reagent preparing device; the reagent preparing device comprising:
a reagent preparing section configured to execute, upon a respective request, a reagent preparing operation in which a quantity of the reagent is prepared from a first liquid and a second liquid different from the first liquid, wherein the first liquid has an expiration date, and the expiration of the first liquid used to prepare the quantity of the reagent determines an expiration date of the quality of the reagent;
a transfer system including pneumatic pumps, valves and conduits operated to transfer the reagent;
a reagent storage container connectable by operation of the transfer system to the measurement section for supply of the reagent to the measurement section and constructed to store a plurality of quantities of the reagent prepared through a series of executions of the reagent preparing operation, the quantities of the reagent stored in the reagent storage container each having its own expiration date;
a data storage operable to store a reagent management list designed to record the expiration dates of the quantities of the reagent being stored in the reagent storage container;
a display; and
a processor and a memory storing a computer program that enables programs the processor to:
operate the transfer system to supply the reagent from the reagent storage container to the measurement section in response to a demand from the measurement section;
execute the reagent preparing operation at the reagent preparing section to prepare the quantity of the reagent and operate the transfer system to supply the quantity of the prepared reagent to the reagent storage container when a remaining amount of the reagent in the reagent storage container becomes less than a predetermined amount;
update the reagent management list stored in the data storage each time the quantity of the prepared reagent is supplied to the reagent storage container, wherein updating the reagent management list comprises deleting an oldest expiration date from the reagent management list and adding in the reagent management list an expiration date of the prepared reagent supplied to the reagent storage container;
determine if any of the expiration dates recorded in the reagent management list has expired; and
operate the display to show a warning upon a determination by the processor that one of the expiration dates recorded in the reagent management list has expired.

2. The reagent preparing device according to claim 1, further comprising a first liquid information reader configured to read first liquid information related to the first liquid, wherein the processor is programmed to generate the expiration date of the first liquid based on the first liquid information read by the first liquid information reader.

3. The reagent preparing device according to claim 1, further comprising a flow-in sensor configured to detect a supply of the quantity of the reagent to the reagent storage container, wherein the processor is programmed to update the reagent management list stored in the data storage.

4. The reagent preparing device according to claim 1, wherein the expiration date of the first liquid includes a post-opening expiration date of the first liquid, and the expiration dates recorded in the reagent management list each include a post-opening expiration date.

5. The reagent preparing device according to claim 4, wherein
the expiration date of the first liquid includes a pre-opening expiration date and the post-opening expiration date of the first liquid, and the expiration dates recorded in the reagent management list each include the pre-opening expiration date and the post-opening expiration date; and
the processor is programmed to display the warning on the display if one of the pre-opening expiration dates and the post-opening expiration dates recorded in the reagent management list expires.

6. The reagent preparing device according to claim 1, further comprising a reagent discarding section in which the quantities of the reagent stored in the reagent storage container are discarded, wherein the processor is programmed to operate the transfer system to discard in the reagent discarding section the entire volume of the quantities of the reagent in the reagent storage container upon a determination by the processor that one of the expiration dates recorded in the reagent management list has expired.

7. The reagent preparing device according to claim 6, wherein
the reagent preparing section includes a mixing container connectable to the reagent storage container by operation of the transfer system and constructed to receive and mix the first liquid and the second liquid inside thereof to prepare the quantity of the reagent; and
the processor is programmed to determine whether or not the expiration date of the quantity of the reagent stored in the mixing container has expired, based on the expiration date of the first liquid used to prepare the quality of the reagent stored in the mixing container.

8. The reagent preparing device according to claim 7, further comprising a liquid discarding section in which the quantity of the reagent stored in the mixing container is discarded, wherein the processor is programmed to operate the transfer system to discard in the liquid discarding section the quantity of the reagent stored in the mixing container upon determination by the processor that the expiration date of the quantity of the reagent stored in the mixing container has expired.

9. The reagent preparing device according to claim 8, wherein the processor is programmed to operate the transfer system to supply the quantity of the reagent from the mixing container to the reagent storage container upon a determination by the processor that the expiration date of the quantity of the reagent stored in the mixing container has not expired.

10. The reagent preparing device according to claim 1, wherein the first liquid is concentrated reagent and the second liquid is water for diluting the concentrated reagent.

11. The reagent preparing device according to claim 1, wherein the reagent preparing section includes a pure water container in which pure water is storable as the second liquid, a concentrated reagent storage container in which concentrated reagent is storable as the first liquid, and a mixing container constructed to mix the pure water and the concentrated reagent inside the mixing container so as to prepare the reagent.

12. A specimen processing system comprising:
a measurement section configured to analyze a specimen using a reagent prepared from a first liquid and a second liquid, different from the first liquid, wherein the first liquid has an expiration date;
a reagent preparing section configured to execution, upon a respective request, a reagent preparing operation in which a quantity of the reagent is prepared that includes a measured amount of the first liquid, wherein the expiration date of the measured amount of the first liquid used to re are the quantity of the reagent determines an expiration date of the quantity of the reagent;
a transfer system including pneumatic pumps, valves and conduits operated to transfer the reagent;
a reagent storage container connectable by operation of the transfer system to the measurement section for supply of the reagent to the measurement section and constructed to store a plurality of quantities of the reagent prepared through a series of executions of the reagent preparing operation, the quantities of the reagent stored in the reagent storage container each having its own expiration date;
a data storage operable to store a reagent management list designed to record the expirations dates of the quantities of the reagent being stored in the reagent storage container;
a display; and
a processor and a memory storing a computer program that programs the processor to:
operate the transfer system to supply the reagent from the reagent storage container to the measurement section in response to a demand from the measurement section;
upon a request, execute the reagent preparing operation at the reagent preparing section to prepare the quantity of the reagent and operate the transfer system to supply the quantity of requested reagent to the reagent storage container when a remaining amount of the reagent in the reagent storage container becomes less than a predetermined amount;
update the reagent management list stored in the data storage each time the quantity of the prepared reagent is supplied to the reagent storage container, wherein updating the reagent management list comprises deleting an oldest expiration date from the reagent management list and adding in the reagent management list an expiration date of the quantity of the requested reagent supplied to the reagent storage container;
determine if any of the expiration dates recorded in the reagent storage container has expired; and
display a warning on the display upon a determination by the processor that one of the liquid expiration dates recorded in the reagent management list has expired.

* * * * *

UNITED STATES PATENT AND TRADEMARK OFFICE
CERTIFICATE OF CORRECTION

PATENT NO.        : 9,207,250 B2
APPLICATION NO.   : 12/730557
DATED             : December 8, 2015
INVENTOR(S)       : Tomoyuki Asahara et al.

Page 1 of 1

It is certified that error appears in the above-identified patent and that said Letters Patent is hereby corrected as shown below:

<u>In the Claims</u>

In column 28, claim 1, line 30, before "programs" delete "enables".

In column 29, claim 6, line 22, before "in the reagent storage" insert --stored--.

In column 30, claim 12, line 14, before "the quantity of the reagent" replace "to re are" with --to prepare--.

Signed and Sealed this
Twenty-eighth Day of June, 2016

Michelle K. Lee
*Director of the United States Patent and Trademark Office*